(12) United States Patent
Crapo et al.

(10) Patent No.: US 12,329,883 B2
(45) Date of Patent: Jun. 17, 2025

(54) SOFT TISSUE REPAIR IMPLANTS COMPRISING HYDROXYBUTYRATE

(71) Applicants: Davol Inc., Warwick, RI (US); University of Pittsburgh—of the Commonwealth System of Higher Education, Pittsburgh, PA (US)

(72) Inventors: Peter Maughan Crapo, North Kingstown, RI (US); Devang Vijay Shah, Franklin, MA (US); Stephen F. Badylak, Pittsburgh, PA (US); George Hussey, Cranberry Township, PA (US); Catalina Pineda Molina, Pittsburgh, PA (US); Brian Sicari, Pittsburgh, PA (US)

(73) Assignees: Davol Inc., Warwick, RI (US); University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 551 days.

(21) Appl. No.: 16/755,219

(22) PCT Filed: Oct. 24, 2018

(86) PCT No.: PCT/US2018/057199
§ 371 (c)(1),
(2) Date: Apr. 10, 2020

(87) PCT Pub. No.: WO2019/084073
PCT Pub. Date: May 2, 2019

(65) Prior Publication Data
US 2020/0261624 A1   Aug. 20, 2020

Related U.S. Application Data

(60) Provisional application No. 62/576,403, filed on Oct. 24, 2017.

(51) Int. Cl.
*A61L 27/54*     (2006.01)
*A61K 31/191*    (2006.01)
*A61L 27/56*     (2006.01)
*A61L 27/58*     (2006.01)

(52) U.S. Cl.
CPC ............ *A61L 27/54* (2013.01); *A61K 31/191* (2013.01); *A61L 27/56* (2013.01); *A61L 27/58* (2013.01); *A61L 2300/21* (2013.01); *A61L 2300/404* (2013.01); *A61L 2430/30* (2013.01); *A61L 2430/34* (2013.01)

(58) Field of Classification Search
None
See application file for complete search history.

(56) References Cited

U.S. PATENT DOCUMENTS

| | | | |
|---|---|---|---|
| 5,017,229 A | 5/1991 | Burns et al. | |
| 5,410,016 A | 4/1995 | Hubbell et al. | |
| 5,527,983 A | 6/1996 | Tadmor et al. | |
| 6,083,524 A | 7/2000 | Sawhney et al. | |
| 6,548,569 B1* | 4/2003 | Williams | A61L 31/06 523/124 |
| 6,610,764 B1 | 8/2003 | Martin et al. | |
| 6,623,749 B2 | 9/2003 | Williams et al. | |
| 6,828,357 B1 | 12/2004 | Martin et al. | |
| 6,838,493 B2 | 1/2005 | Williams et al. | |
| 7,179,883 B2 | 2/2007 | Williams et al. | |
| 7,244,442 B2 | 7/2007 | Williams et al. | |
| 2004/0234576 A1 | 11/2004 | Martin et al. | |
| 2005/0244455 A1 | 11/2005 | Greenawalt | |
| 2013/0309275 A1* | 11/2013 | Carter | B29C 45/0055 514/23 |
| 2014/0343580 A1 | 11/2014 | Priewe | |
| 2015/0056131 A1 | 2/2015 | Bernasconi et al. | |
| 2016/0082160 A1 | 3/2016 | Martin et al. | |
| 2017/0157302 A1 | 6/2017 | Cotton et al. | |
| 2017/0216018 A1 | 8/2017 | Limem et al. | |

FOREIGN PATENT DOCUMENTS

| | | |
|---|---|---|
| CN | 101327335 A | 12/2008 |
| CN | 101347636 A | 1/2009 |
| JP | 7-275344 A | 10/1995 |
| WO | WO 2004/101002 A2 | 11/2004 |
| WO | WO 2017/068415 A1 | 4/2017 |

OTHER PUBLICATIONS

International Search Report and Written Opinion mailed Dec. 21, 2018, for Application No. PCT/US2018/057199.
International Preliminary Report on Patentability mailed May 7, 2020, for Application No. PCT/US2018/057199.
Scott et al., Evaluation of a fully absorbable poly-4-hydroxybutyrate/absorbable barrier composite mesh in a porcine model of ventral hernia repair. Surg Endosc. Sep. 2016;30(9):3691-701. doi: 10.1007/s00464-016-5057-9. Epub Jul. 1, 2016.
PCT/US2018/057199, Dec. 21, 2018, International Search Report and Written Opinion.
PCT/US2018/057199, May 7, 2020, International Preliminary Report on Patentability.

(Continued)

*Primary Examiner* — David J Blanchard
*Assistant Examiner* — Daniel F Coughlin
(74) *Attorney, Agent, or Firm* — Wolf, Greenfield & Sacks, P.C.

(57) ABSTRACT

Articles and methods involving soft tissue repair implants comprising 2-hydroxybutyrate, 3-hydroxybutyrate, 4-hydroxybutyrate, and/or their conjugate acids are generally provided. The 2-hydroxybutyrate, 3-hydroxybutyrate, 4-hydroxybutyrate, and/or the conjugate acid(s) of 2-hydroxybutyrate, 3-hydroxybutyrate, and 4-hydroxybutyrate may be provided in a therapeutically-effective amount for reducing or preventing microbial infection.

19 Claims, 12 Drawing Sheets

(56) References Cited

OTHER PUBLICATIONS

Plymale et al., Ventral hernia repair with poly-4-hydroxybutyrate mesh. Surg Endosc. Apr. 2018;32(4):1689-1694. doi: 10.1007/s00464-017-5848-7. Epub Sep. 15, 2017.

Ray et al., Biomedical Applications of Polyhydroxyalkanoates. Indian J Microbiol. Sep. 2017;57(3):261-269. doi: 10.1007/s12088-017-0651-7. Epub Apr. 22, 2017.

Sakai et al., Studies on Chemotherapy of Trichophyton infections. II. Antifungal properties of halogen phenol esters and halogen phenol derivatives. J Sci Res Inst. 1954;48:38-48.

* cited by examiner

SOFT TISSUE REPAIR IMPLANTS COMPRISING HYDROXYBUTYRATE

RELATED APPLICATIONS

The present invention is a national stage filing under 35 U.S.C. § 371 of international PCT application, PCT/US2018/057199, filed Oct. 24, 2018, which claims priority under 35 U.S.C. § 119(e) to U.S. provisional patent application, U.S. Ser. No. 62/576,403, filed Oct. 24, 2017, the entire contents of each of which are which is incorporated herein by reference.

FIELD

Articles and methods involving soft tissue repair implants comprising a hydroxybutyrate and/or a conjugate acid of a hydroxybutyrate for reducing infection.

BACKGROUND

Soft tissue repair implants may be useful for a wide variety of surgical applications, such as hernia repair. However, surgical processes performed during the implantation of soft tissue repair implants into a patient may expose the patient to one or more pathogens, which may cause infection. Accordingly, soft tissue repair implants that have antimicrobial properties and associated methods for treating soft tissues are desirable.

SUMMARY

Articles and methods involving soft tissue repair implants comprising a hydroxybutyrate (e.g., 2-hydroxybutyrate, 3-hydroxybutyrate, 4-hydroxybutyrate), and/or their conjugate acids are generally provided.

In certain embodiments, soft tissue repair implants are provided. The soft tissue repair implant may comprise a body portion and a therapeutically-effective amount of at least one of a hydroxybutyrate and a conjugate acid of a hydroxybutyrate for reducing or preventing microbial infection. The therapeutically-effective amount of at least one of a hydroxybutyrate and a conjugate acid of a hydroxybutyrate for reducing or preventing microbial infection may be included in, on, or otherwise associated with the body portion.

In other embodiments, methods are provided. The method may comprise implanting a soft tissue repair implant at a soft tissue site of a patient, wherein the soft tissue repair implant comprises a body portion and a therapeutically-effective amount of at least one of a hydroxybutyrate and a conjugate acid of a hydroxybutyrate for reducing or preventing microbial infection in, on, or otherwise associated with the body portion.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Articles and methods related to soft tissue repair implants are generally provided. In some embodiments, a soft tissue repair implant may include a hydroxybutyrate (e.g., 2-hydroxybutyrate, 3-hydroxybutyrate, 4-hydroxybutyrate), and/or a conjugate acid of a hydroxybutyrate (hereinafter referred to as hydroxybutyrates and their conjugate acids). The one or more hydroxybutyrates and/or their conjugate acids may provide one or more benefits to a patient into which a soft tissue repair implant is implanted. For example, hydroxybutyrates and/or their conjugate acids may increase the expression of antimicrobial polypeptides such as cathelicidin LL-37 and beta-defensins. As another example, hydroxybutyrates and/or their conjugate acids may modulate inflammation (reduce or increase inflammation depending upon the application). When provided to a patient during surgery (e.g., as part of a soft tissue repair implant), hydroxybutyrates and/or their conjugate acids may exhibit one or more of these beneficial properties, may reduce or prevent the incidence of surgical infection, the severity of surgical infection, the amount of pain at the surgical site, and/or may modulate an inflammatory response at the surgical site.

As described in more detail below, the hydroxybutyrate and/or conjugate acid of the hydroxybutyrate may be present in the soft tissue repair implant in the form of a monomer (e.g., as an alkali metal salt of a hydroxybutyrate, and/or as a conjugate acid of a hydroxybutyrate) or as an oligomer. The hydroxybutyrate and/or conjugate acid of the hydroxybutyrate may be present in the soft tissue repair implant in a therapeutically-effective amount for reducing or preventing microbial infection.

The one or more hydroxybutyrates and/or their conjugate acids may be associated with the soft tissue repair implant in any suitable manner. For instance, in some embodiments the one or more hydroxybutyrates and/or their conjugate acids may be coated onto all or a portion of the soft tissue repair implant. In certain embodiments, the one or more hydroxybutyrates and/or their conjugate acids may be incorporated into the soft tissue repair implant by impregnation, by forming, by casting, or by extrusion. Other configurations are also possible.

Figure 1:
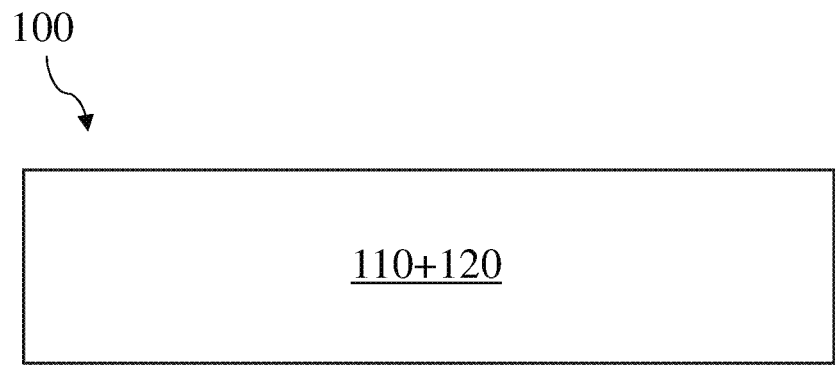
FIG. 1 is a cross-sectional schematic illustration of a soft tissue repair implant, according to some embodiments of the invention.

In some embodiments, a soft tissue repair implant as described herein may comprise a body portion configured to repair a soft tissue defect and a hydroxybutyrate and/or conjugate acid of a hydroxybutyrate. In some embodiments, the body portion may have a planar form. In other embodiments, the body portion may be in the form of a three-dimensional shape, or may be a combination of a planar form and a three-dimensional shape. In certain embodiments, the body portion may be pre-shaped to conform to an anatomical placement or the body portion may be conformable to an anatomical placement after insertion. FIG. 1 shows one non-limiting embodiment of a soft tissue repair implant 100 which comprises a body portion 110 and a hydroxybutyrate and/or conjugate acid of hydroxybutyrate 120. As will be described in further detail below, the hydroxybutyrate and/or conjugate acid thereof may be provided in a variety of suitable forms in the soft tissue repair implant. In some embodiments, such as that shown in FIG. 1, the hydroxybutyrate and/or the conjugate acid of a hydroxybutyrate may be provided as a component of the body portion (e.g., integrated with the body portion such as, for example, by impregnation within the body portion, coating of the body portion, etc.).

The soft tissue repair implant may comprise any suitable hydroxybutyrate and/or any conjugate acid of a hydroxybutyrate. In some embodiments, the soft tissue repair implant comprises 4-hydroxybutyrate (GHB or 4HB) or 4-hydroxybutyric acid (the conjugate acid of 4-hydroxybutyrate). In some embodiments, the soft tissue repair implant comprises both 4-hydroxybutyrate and 4-hydroxybutyric acid. In some embodiments, the soft tissue repair implant comprises one or more of 2-hydroxybutyrate, 3-hydroxybutyrate, 2-hydroxybutyric acid, and 3-hydroxybutyric acid. References to hydroxybutyrates and their conjugate acids should be understood to refer to compositions that include one type of hydroxybutyrate, include one type of conjugate acid of a hydroxybutyrate, include a mixture of a single type of hydroxybutyrate and its conjugate acid, include a mixture of hydroxybutyrates, include a mixture of conjugate acids of hydroxybutyrates, or include a mixture of hydroxybutyrates and hydroxybutyrate conjugate acids.

In some embodiments, the hydroxybutyrate may be in ionic form (e.g., the soft tissue repair implant may comprise a salt of a hydroxybutyrate). For example, a hydroxybutyrate may be in an anion form and the anionic hydroxybutyrate may have a variety of suitable counter ions. The hydroxybutyrate salt may be, for example, a monovalent salt, a divalent salt, or a trivalent salt. In some embodiments, the hydroxybutyrate salt may be an alkali metal salt or an alkaline earth metal salt. The alkali metal salt may be, for example, a sodium salt of a hydroxybutyrate and/or a potassium salt of a hydroxybutyrate. In some embodiments, the soft tissue repair implant comprises a salt (e.g., an alkali metal salt, an alkaline earth metal salt) of 4-hydroxybutyrate. In some embodiments, the soft tissue repair implant comprises a salt (e.g., an alkali metal salt, an alkaline earth metal salt) of 2-hydroxybutyrate. In some embodiments, the soft tissue repair implant comprises a salt (e.g., an alkali metal salt, an alkaline earth metal salt) of 3-hydroxybutyrate. Suitable combinations thereof are also possible.

In some embodiments, the soft tissue repair implant may comprise a hydroxybutyrate and/or a conjugate acid of a hydroxybutyrate that is in the form of a monomer that is not covalently bonded to any other species. For example, the hydroxybutyrate may be present as an anion (e.g., as a component of a salt, i.e., in salt form), or the conjugate acid of the hydroxybutyrate may be present as a free acid (i.e., in acid form). In other embodiments, the soft tissue repair implant may comprise a hydroxybutyrate and/or a conjugate acid of a hydroxybutyrate that is chemically bonded to other monomers to form an oligomer. In yet other embodiments, the soft tissue repair implant may comprise a hydroxybutyrate and/or a conjugate acid of a hydroxybutyrate that is chemically bonded (e.g., covalently bonded, ionically bonded, bonded by van der Waals forces) to a polymer, and/or is chemically bonded (e.g., covalently bonded, ionically bonded, bonded by van der Waals forces) to a solid material (e.g., a solid surface, a fiber).

When a hydroxybutyrate and/or a conjugate acid of a hydroxybutyrate is in the form of a monomer in an oligomer, the oligomer may be a variety of suitable oligomers. In some embodiments, the oligomer may be a homo-oligomer. In other words, the oligomer may be formed exclusively from a single type of monomer (e.g., from 4-hydroxybutyrate, from a single type of hydroxybutyrate, from a single type of conjugate acid of a hydroxybutyrate). In other embodiments, the oligomer may be a co-oligomer, or an oligomer formed from more than one type of monomer. Co-oligomers may be formed exclusively from hydroxybutyrate monomers and/or monomers that are conjugate acids of hydroxybutyrates (e.g., a co-oligomer may be formed exclusively from 4-hydroxybutyrate monomers and 3-hydroxybutyrate monomers, or exclusively from 4-hydroxybutyrate monomers and 2-hydroxybutyrate monomers), or co-oligomers may comprise monomers that are non-hydroxybutyrate monomers (e.g., short chain fatty acid monomers, esters, saccharides). The arrangement of different types of monomers with respect to each other in the co-oligomer may be selected as desired. For example, the co-oligomer may be a block co-oligomer, may be a blocky co-oligomer, or may be a random co-oligomer. The relative ratios of the monomers making up the co-oligomer may also be selected as desired.

In some embodiments, a hydroxybutyrate and/or a conjugate acid of a hydroxybutyrate is in the form of a branched polymer, a non-branched polymer, or a dendrimer.

A hydroxybutyrate and/or a conjugate acid of a hydroxybutyrate described herein (e.g., a polymer, oligomer, co-oligomer, or other molecule comprising the hydroxybutyrate and/or conjugate acid of the hydroxybutyrate) may have any suitable molecular weight (e.g., weight average molecular weight). In some embodiments, the hydroxybutyrate and/or the conjugate acid of a hydroxybutyrate has a molecular weight (e.g., weight average molecular weight) of less than or equal to 250 kDa, less than or equal to 200 kDa, less than or equal to 150 kDa, less than or equal to 100 kDa, less than or equal to 90 kDa, less than or equal to 75 kDa, less than or equal to 50 kDa, less than or equal to 25 kDa, less than or equal to 10 kDa, less than or equal to 5 kDa, less than or equal to 2 kDa, less than or equal to 1 kDa, less than or equal to 500 Da, or less than or equal to 250 Da. In some embodiments, the hydroxybutyrate and/or the conjugate acid of a hydroxybutyrate has a molecular weight (e.g., weight average molecular weight) of at least 100 Da, at least 250 Da, at least 500 Da, at least 1 kDa, at least 2 kDa, at least 5 kDa, at least 10 kDa, at least 25 kDa, at least 50 kDa, at least 100 kDa, or at least 200 kDa. Combinations of the above-referenced ranges are also possible. Other ranges are also possible. The molecular weight (e.g., weight average molecular weight) may be measured by gel permeation chromatography.

When a hydroxybutyrate and/or a conjugate acid of a hydroxybutyrate is chemically bonded to a polymer, the polymer may be any suitable polymer. In some embodiments, the polymer is not a homopolymer of a hydroxybutyrate or a homopolymer of a conjugate acid of a hydroxybutyrate. For example, the polymer may be a copolymer of a hydroxybutyrate monomer and a non-hydroxybutyrate monomer. In certain embodiments, the hydroxybutyrate and/or conjugate acid of a hydroxybutyrate may be a side chain that is chemically grafted to a polymer. In certain embodiments, the polymer to which the hydroxybutyrate is chemically bonded does not include a hydroxybutyrate itself (e.g., prior to bonding). Examples of suitable polymers are provided below.

When a hydroxybutyrate and/or a conjugate acid of a hydroxybutyrate is chemically bonded to a solid material (e.g., of a body portion), it may be bonded to any suitable type of solid material (e.g., resorbable materials, non-resorbable materials). For example, the hydroxybutyrate and/or the conjugate acid of a hydroxybutyrate may be chemically bonded to a metal, ceramic, polymer, and/or composite. Exemplary polymers include, but are not limited to, resorbable polymers such as poly(glycolic acid), poly(lactic acid), poly(dioxanone), poly(caprolactone), polyhydroxyalkanoate (e.g., poly-2-hydroxybutyrate, poly-3-hydroxybuytrate, poly-4-hydroxybutyrate), calcium alginate, poly(glactin) (VICRYL™), and poly(glycolic acid) (DEXON™). In certain cases, one or more non-resorbable materials such as polypropylene and poly(ethylene terephthalate) can be used.

When a hydroxybutyrate and/or a conjugate acid of a hydroxybutyrate is chemically bonded to a solid material (e.g., of a body portion), it may be bonded to any suitable portion of the solid material. For example, the hydroxybutyrate and/or the conjugate acid of a hydroxybutyrate may be chemically bonded to a surface of the solid material, such as to the surface of a layer (e.g., an outer surface, fibers in or on a layer).

As another example, the hydroxybutyrate and/or the conjugate acid of a hydroxybutyrate may be chemically bonded to the solid material within its interior (e.g., an interior surface). In some embodiments, the solid material is encapsulated by the hydroxybutyrate and/or the conjugate acid of a hydroxybutyrate.

In some embodiments, the soft tissue repair implant comprises a hydroxybutyrate or a conjugate acid of a hydroxybutyrate in a therapeutically-effective amount for reducing microbial infection. In some embodiments, the hydroxybutyrate or conjugate acid of a hydroxybutyrate provided in a therapeutically effective amount is 4-hydroxybutyrate, 4-hydroxybutyric acid, or a mixture thereof. In some embodiments, the hydroxybutyrate or conjugate acid of a hydroxybutyrate provided in a therapeutically effective amount is 2-hydroxybutyrate, 2-hydroxybutyric acid, or a mixture thereof. In some embodiments, the hydroxybutyrate or conjugate acid of a hydroxybutyrate provided in a therapeutically effective amount is 3-hydroxybutyrate, 3-hydroxybutyric acid, or a mixture thereof. In some embodiments, a combination of 4-, 2-, and 3-hydroxybutyrates are possible.

In some embodiments, the soft tissue repair implant may be configured to release a hydroxybutyrate (e.g., 4-hydroxybutyrate, 2-hydroxybutyrate, 3-hydroxybutyrate), a conjugate acid of a hydroxybutyrate (e.g., 4-hydroxybutyric acid, 2-hydroxybutyric acid, 3-hydroxybutyric acid), and/or a combination of hydroxybutyrates and/or their conjugate acids (e.g., a mixture of 4-hydroxybutyrate and 4-hydroxybutyric acid, other mixtures of hydroxybutyrates described herein) at a certain release rate when positioned adjacent soft tissue. In some such embodiments, the hydroxybutyrate may be a part of a body portion, a coating, a solid portion, and/or a layer of a soft tissue repair implant as described herein.

In some embodiments, the soft tissue repair implant may be configured to release a hydroxybutyrate, a conjugate acid of a hydroxybutyrate, and/or a combination of hydroxybutyrates and/or their conjugate acids (e.g., a mixture of 4-hydroxybutyrate and 4 hydroxybutyric acid, other mixtures of hydroxybutyrates described herein) over a certain period of time when positioned adjacent soft tissue. The release time may be, for example, at least 10 days, at least 20 days, at least 30 days, at least 45 days, at least 3 months, at least 6 months, at least 9 months, at least 1 year, or at least 2 years. In some embodiments, the release time is less than or equal to 2 years, less than or equal to 1 year, less than or equal to 9 months, less than or equal to 6 months, less than or equal to 3 months, less than or equal to 45 days, or less than or equal to 10 days. Combinations of the above-referenced ranges are also possible. Other ranges are also possible. In some such embodiments, the hydroxybutyrate may be a part of a body portion, a coating, a solid portion, and/or a layer of a soft tissue repair implant as described herein.

Figure 2A:
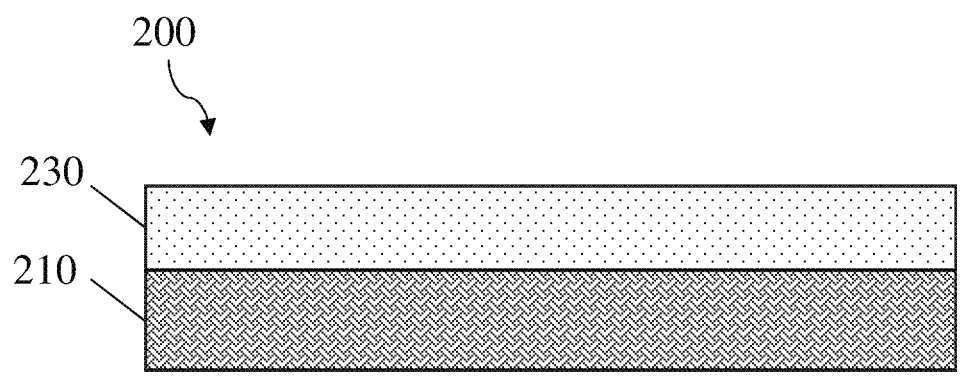
FIG. 2A is a cross-sectional schematic illustration of a soft tissue repair implant comprising a body portion and a coating, according to some embodiments of the invention.

In some embodiments, a soft tissue repair implant may comprise a hydroxybutyrate and/or a conjugate acid of a hydroxybutyrate that is disposed on and/or in a body portion. In certain embodiments, the hydroxybutyrate and/or the conjugate acid of a hydroxybutyrate is a part of a coating that coats at least a portion of a body portion. A non-limiting embodiment of a soft tissue repair implant comprising a coating of a hydroxybutyrate and/or a conjugate acid of a hydroxybutyrate is shown in FIG. 2A. FIG. 2A depicts a soft tissue repair implant 200 comprising a body portion 210 and a coating 230. Such a coating may be applied to some but not all of the surfaces of the soft tissue repair implant, or to all of the surfaces of the soft tissue repair implant. For example, as described in more detail below, at least a portion of the body portion may be immersed in a liquid containing the hydroxybutyrate and/or the conjugate acid of a hydroxybutyrate and then dried to form the coating. The coating may only coat a portion (but not all) of the body portion, such as an upper surface of the body portion and/or a lower surface of the body portion, or the coating may coat all of the surfaces of the body portion. In other embodiments a coating (e.g., a film or sheet) may be formed separately and then combined (e.g., by collation, by adhesives) with the body portion such that the coating is at least adjacent to the body portion.

Figure 2B:
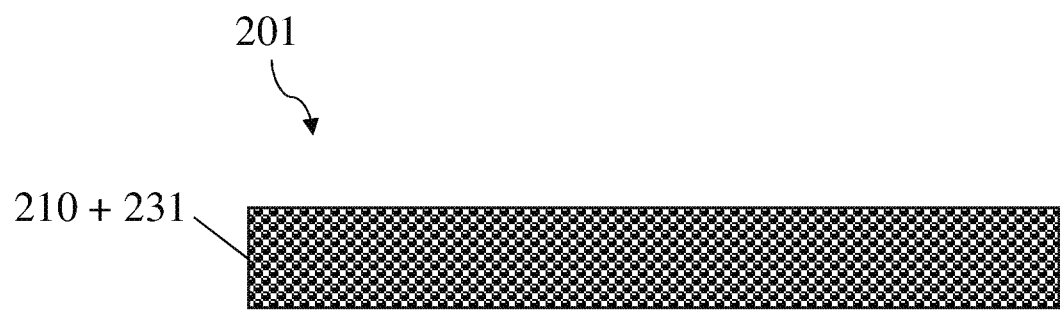
FIG. 2B is a cross-sectional schematic illustration of a soft tissue repair implant comprising a body portion and a coating, according to some embodiments of the invention.

In some embodiments, a soft tissue repair implant may comprise a hydroxybutyrate and/or a conjugate acid of a hydroxybutyrate that is a component of a coating that coats an interior of a body portion (e.g., an interior of a body portion layer). A non-limiting embodiment of a soft tissue repair implant comprising a coating comprising a hydroxybutyrate and/or a conjugate acid of a hydroxybutyrate that coats an interior of a body portion is shown in FIG. 2B. FIG. 2B depicts a soft tissue repair implant 201 comprising body portion 210 and a coating 231 which coats an interior of the body portion. For instance, in some embodiments in which the body portion comprises pores or fibers, the coating may conformally coat the pores or the fibers within the body portion. For example, the entire body portion may immersed in a liquid containing the hydroxybutyrate and/or the conjugate acid of a hydroxybutyrate and then dried to form an impregnated coated body portion. In another example, a hydroxybutyrate and/or a conjugate acid of a hydroxybutyrate (e.g., in the form of a monomer, in the form of an oligomer) may be bonded (e.g., covalently bonded) to an interior surface of the body portion.

In some embodiments, a soft tissue repair implant may comprise a hydroxybutyrate and/or a conjugate acid of a hydroxybutyrate that is a component of a foam.

In some embodiments, a soft tissue repair implant may comprise a hydroxybutyrate and/or a conjugate acid of a hydroxybutyrate that is a component of a hydrogel (e.g., a hydrogel coating). For example, the hydrogel may be similar or identical to the hydrogel described in U.S. Patent Pub. No. 2005/0244455, incorporated herein by reference in its entirety. The hydrogel may comprise at least one polyanionic polysaccharide modified by reaction with carbodiimide. In some embodiments, the hydrogel includes a crosslinked polymer hydrogel alone or in combination with at least one polyanionic polysaccharide modified by reaction with carbodiimide. The hydrogel may include one or more hydrophilic blocks, one or more biodegradable blocks, and one or more crosslinking blocks. The hydrogel may be formed by polymerization of monomers including photopolymerizable poly(ethylene glycol)-trimethylene carbonate/lactate multi-block polymers endcapped with acrylate esters. The polyanionic polysaccharide modified by reaction with carbodiimide includes carbodiimide-modified hyaluronic acid and carbodiimide-modified carboxymethylcellulose.

When present, a hydrogel may be prepared from one or more components selected from hyaluronic acids and any of its salts, carboxymethylcellulose and any of its salts, oxidized regenerated cellulose, collagen, gelatin, phospholipids, and the first and second polymer systems described below, as well as any crosslinked or derivatized forms thereof. In some embodiments, a hydrogel (e.g., a hydrogel coating) is made from a material capable of forming a hydrogel when contacted with an aqueous fluid, such as saline, phosphate buffer, or a bodily fluid.

In some embodiments, a hydrogel composition (e.g., a hydrogel coating composition) comprises a mixture of at least two polymer systems. The first polymer system includes a crosslinked biodegradable multi-block polymer hydrogel having a three-dimensional polymer network. The second polymer system comprises at least one polyanionic polysaccharide modified by reaction with a carbodiimide compound.

The hydrogel of the first polymer system, when present, may comprise hydrophilic blocks, biodegradable blocks, and crosslinking blocks formed during the polymerization of macromers. The macromers may be large molecules that comprise at least one hydrophilic block, at least one biodegradable block and at least one polymerizable group. One or more of these blocks may be polymeric in nature. At least one of the biodegradable blocks may comprise a linkage based on a carbonate or ester group, and the macromers can contain other degradable linkages or groups in addition to carbonate or ester groups. Suitable macromers to form polymer hydrogels and methods of preparing them have been described in U.S. Pat. Nos. 6,083,524 and 5,410,016, the disclosures of which are incorporated herein by reference.

Suitable hydrophilic polymeric blocks include those which, prior to incorporation into the macromer, are water-soluble such as poly(ethylene glycol), poly(ethylene oxide), partially or fully hydrolyzed poly(vinyl alcohol), poly(vinylpyrrolidone), poly(ethyloxazoline), poly(ethylene oxide)-co-poly(propylene oxide) block copolymers (poloxamers and meroxapols), poloxamines, carboxymethyl cellulose, hydroxyalkylated celluloses such as hydroxyethyl cellulose and methylhydroxypropyl cellulose, polypeptides, polynucleotides, polysaccharides or carbohydrates such as Ficoll® polysucrose, hyaluronic acid, dextran, heparin sulfate, chondroitin sulfate, heparin, or alginate, and proteins such as gelatin, collagen, albumin, or ovalbumin. The preferred hydrophilic polymeric blocks are derived from poly(ethylene glycol) and poly(ethylene oxide).

In certain embodiments, a hydrogel may comprise biodegradable blocks that are hydrolyzable under in vivo conditions. Biodegradable blocks can include polymers and oligomers of hydroxy acids, carbonates or other biologically degradable polymers that yield materials that are non-toxic or present as normal metabolites in the body. Examples of suitable oligomers or polymers of hydroxy acids are poly(glycolic acid), also called polyglycolate, poly(DL-lactic acid) and poly(L-lactic acid), also called polylactate. Other useful materials include poly(amino acids), poly(anhydrides), poly(orthoesters), and poly(phosphoesters). Polylactones such as poly(epsilon-caprolactone), poly(delta-valerolactone), and poly(gamma-butyrolactone), for example, are also useful. Certain carbonates are derived from the cyclic carbonates, which can react with hydroxy-terminated polymers without release of water. Suitable carbonates are derived from ethylene carbonate (1,3-dioxolan-2-one), propylene carbonate (4-methyl-1,3-dioxolan-2-one), trimethylene carbonate (1,3-dioxan-2-one) and tetramethylene carbonate (1,3-dioxepan-2-one).

Polymerizable groups, when present, may be reactive functional groups that have the capacity to form additional covalent bonds that result in macromer interlinking. Polymerizable groups specifically include groups capable of polymerizing via free radical polymerization and groups capable of polymerizing via cationic or heterolytic polymerization. Suitable groups include, but are not limited to, ethylenically or acetylenically unsaturated groups, isocyanates, epoxides (oxiranes), sulfhydryls, succinimides, maleimides, amines, imines, amides, carboxylic acids, sulfonic acids and phosphate groups. Ethylenically unsaturated groups include vinyl groups such as vinyl ethers, N-vinyl amides, allyl groups, unsaturated monocarboxylic acids or their esters or amides, unsaturated dicarboxylic acids or their esters or amides, and unsaturated tricarboxylic acids or their esters or amides. Unsaturated monocarboxylic acids include acrylic acid, methacrylic acid and crotonic acid or their esters or amides. Unsaturated dicarboxylic acids include maleic, fumaric, itaconic, mesaconic or citraconic acid or their esters or amides. Unsaturated tricarboxylic acids include aconitic acid or their esters or amides. Polymerizable groups may also be derivatives of such materials, such as acrylamide, N-isopropylacrylamide, hydroxyethylacrylate, hydroxyethylmethacrylate, and analogous vinyl and allyl compounds.

When present, polymerizable groups are preferably located at one or more ends of a macromer. Alternatively, the polymerizable groups can be located within the macromer. At least a portion of the macromers may contain more than one reactive group per molecule so that the resulting hydrophilic polymer can be crosslinked to form a gel. Macromers having two or more polymerizable groups per molecules are referred to herein as crosslinkers. The minimal proportion of crosslinkers required will vary depending on the desired properties of the hydrogel to be formed and the initial macromer concentration in solution. The proportion of crosslinkers in the macromer solution can be as high as about 100% of all macromers in the solution. For example, the macromers may include at least 1.02 polymerizable groups on average, or the macromers may each include two or more polymerizable groups on average. Poloxamines, an example of water-soluble polymer component suitable to form a hydrophilic block, have four arms and thus may readily be modified to include four polymerizable groups.

Examples of suitable macromers are illustrated below:

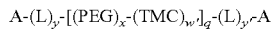

where the polyethylene glycol repeat unit is —($CH_2$—$CH_2$—O)$_x$— or (PEG)$_x$, the trimethylene carbonate repeat unit is —(C(O)—O—($CH_2$)$_3$—O)$_w$— or (TMC)$_w$; the lactic acid residue is —(O—CH($CH_3$)—CO)$_y$— or (L)$_y$; acrylate residue is $CH_2$=CH—CO— or A, and q, w, w', y, y' and x are integers.

Polymerization of the macromers can be initiated by photochemical means, by non-photochemical like redox (Fenton chemistry) or by thermal initiation (peroxide etc). Suitable photochemical means include exposure of the macromer solution to visible light or UV light in the presence of a photoinitiator such as UV or light sensitive compounds such as dyes, including eosin Y.

Polymerization of the macromers may be conducted in the presence of small amounts of monomers which act as accelerant of the polymerization reaction. In some embodiments, the monomers represent 2% or less of the total content of the polymerizable material, 1% or less, and/or about 4,000 ppm. An example of an accelerant is vinyl caprolactam.

In the discussion below and the examples, macromers may be designated by a code of the form xxkZnAm, where xxk represents the molecular weight in Daltons of the backbone polymer, which is polyethylene glycol ("PEG") unless otherwise stated, with x as a numeral and k as the multiplier for thousands; Z designates the molecular unit from which the biodegradable block is derived from and may take the value one or more of L, G, D, C, or T, where L is for lactic acid, G is for glycolic acid, D is for dioxanone, C is for caprolactone, T is for trimethylene carbonate; n is the average number of degradable groups randomly distributed on each end of the backbone polymer; A is for acrylate and m for the number of polymerizable groups per macromer molecules. Thus 20kTLA2 is a macromer with a $20\times10^3$ Da polyethylene glycol core with an average of first trimethylene carbonate residues (7 or more residues per macromers, in average about 12) and lactic acid residues (5 or less residues per macromers) sequentially extending on both ends of the glycol core and randomly distributed between both ends then terminated with 2 acrylate groups.

The second polymer system may comprise at least one polyanionic polysaccharide modified by a carbodiimide. Methods of preparation of these modified polymers have been described in U.S. Pat. Nos. 5,017,229 and 5,527,983, the entire disclosures of which are incorporated herein by reference.

Suitable polyanionic polysaccharides may be selected from one or more of the following, hyaluronic acid, carboxymethyl cellulose, carboxymethyl amylose, carboxymethyl chitosan, chondroitin sulfate, dermatan sulfate, heparin, heparin sulfate, alginic acid, and any of their salts, including sodium, potassium, magnesium, calcium, ammonium or mixtures thereof.

The polyanionic polysaccharides, when present, may be modified by reaction with a carbodiimide to form N-acyl urea derivatives and render them water insoluble, however, they remain very hydrophilic and thus absorb water to form gels also referred to as hydrogels. The reaction conditions with carbodiimides are well described in the cited patents above. Preferred carbodiimides are those that exhibit water solubility, such as 1-(3-dimethylaminopropyl)-3-ethyl-carbodiimide (EDC) or 1-ethyl-3-(3-dimethylaminopropyl)-carbodiimide methiodide (ETC).

After reaction with carbodiimide, the modified polyanionic polysaccharide compositions may be dried to less than about 20% moisture content, in some cases to about 9% moisture content, and stored in powder form.

To prepare the hydrogel compositions, the modified polyanionic polysaccharide composition may be rehydrated in buffer alone to form a fluid gel before mixing with the macromer solution of the second polymer system. The hydrogel composition may also be prepared by rehydrating the modified polyanionic polysaccharide composition in the buffer solution of the macromer solution of the second polymer system, thereby forming a fluid gel that comprises both polymer systems. The fluid gel may then be cast in a dish having the desired shape and exposed to polymerizing condition, such a UV or visible light to form a polymeric material. Once the macromers in the fluid gel have polymerized, the polymeric material forms a hydrated soft rubbery material that has improved handling properties and is resistant to tear. The barrier composition may be polymerized into desired shape articles like sheets, discs, tubes or rods by selecting appropriate casts or by extrusion.

The hydrogel composition may be further dried for packaging and then rehydrated prior to implantation into the body of a patient (such as a human or animal such as non-human mammals). The hydrogel composition or shaped article may be dried to a moisture content of less than about 5%, and/or less than about 2% in a convection oven to form a film or membrane, and/or freeze-dried under a vacuum to form a foam. The hydrogel composition may have utility in treating or preventing complications from surgeries (e.g., it may prevent the formation of adhesions).

The hydrogel composition may then be deposited on the surface of a body portion (e.g., on the surface of a body portion layer) as a fluid and then dried by any known method. In embodiments in which hydrogel composition is in the form of a film or a foam, the hydrogel composition can be laminated and/or stitched to the body portion by any known method. In embodiments in which the hydrogel composition is formed from a solution including macromers (e.g., a fluid gel), the hydrogel composition can be deposited on the body portion by placing the body portion in the fluid gel and initiating polymerization. Hydrophobic body portions will float on the surface of the fluid gel. Less hydrophobic body portions, such as body portions having polar groups (e.g., esters, amides, ketones, and carbonates), may penetrate through the surface into the fluid gel to a certain extent such that polymerization of functional groups on the macromers in the presence of the body portion provides for greater adherence of the hydrogel composition to the body portion. In multilayered body portions where one layer is less hydrophobic than the other, when placing the less hydrophobic body portion layer over the fluid gel, the layer on that side of the body portion may penetrate the fluid gel, while the hydrophobic layer on the other side of the multilayered body portion may float over the fluid gel. Once the composition is polymerized, a portion of the polymer network entraps the less hydrophobic layer of the body portion and may, for example, provide added adhesion strength of a barrier layer.

Once applied to the body portion(s) and/or layer(s), the hydrogel composition may be dried for long-term storage and packaging, then rehydrated prior to implantation into the body of a patient.

As described herein, in some embodiments a tissue repair implant may include a coating comprising a hydroxybutyrate and/or a conjugate acid of a hydroxybutyrate. The coating may provide one or more further benefits in addition to serving as a source of a hydroxybutyrate and/or a conjugate acid of a hydroxybutyrate (e.g., for reducing or preventing microbial infection). For example, the coating may reduce and/or prevent adhesions with the soft tissue repair implant. In other embodiments, the coating may promote adhesions with the soft tissue repair implant or between adjacent tissue surfaces. In some embodiments, the coating may be resorbable over a period of time that is shorter than the period of time over which one or more of the body portion(s) (e.g., one or more body portion layer(s)) is resorbable. In some such embodiments, by the time the coating has been absorbed, a surgical opening adjacent the body portion(s) (e.g., adjacent the body layer(s)) has healed to an extent (e.g., a new peritoneal surface has formed over the surgical opening) that the likelihood of adhesions forming between soft tissue and the body portion(s) (e.g., between soft tissue and the body layer(s)) is lessened.

In certain embodiments, the one or more hydroxybutyrates and/or their conjugate acids may be incorporated into the soft tissue repair implant, e.g., by impregnation, by forming, by casting, by extrusion, or in other suitable manner in a therapeutically-effective amount for reducing or preventing microbial infection.

When present, a soft tissue implant may comprise the hydroxybutyrate and/or conjugate acid of a hydroxybutyrate in a variety of suitable amounts. In some embodiments, the implant includes the hydroxybutyrate and/or conjugate acid of a hydroxybutyrate (e.g., a mixture of 4-hydroxybutyrate and 4-hydroxybutyric acid, other mixtures of hydroxybutyrates described herein) in an amount of at least 1 wt %, at least 5 wt %, at least 10 wt %, at least 15 wt %, at least 25 wt %, at least 50 wt %, at least 75 wt %, or at least 90 wt % of the implant. In some embodiments, the implant includes the hydroxybutyrate and/or conjugate acid of a hydroxybutyrate in an amount of less than or equal to 100 wt %, less than or equal to 75 wt %, less than or equal to 50 wt %, less than or equal to 25 wt %, less than or equal to 10 wt %, or less than or equal to 5 wt % of the implant. Combinations of the above-referenced ranges are also possible. Other ranges are also possible. In some embodiments in which the hydroxybutyrate and/or conjugate acid is present in the form of a body portion, a coating, a solid portion, and/or a layer of a soft tissue repair implant, the body portion, coating, solid portion, and/or layer may include the hydroxybutyrate and/or conjugate acid in an amount specified in one or more of the ranges noted above.

In some embodiments, a soft tissue repair implant may comprise a hydroxybutyrate and/or a conjugate acid of a hydroxybutyrate, and may further comprise one or more additional components. Non-limiting examples of additional components include compounding agents, such as compounding polymers, surfactants, acidic catalysts or basic catalysts to facilitate hydrolysis of the hydroxybutyrate, short chain fatty acids, and complexing agents. Non-limiting examples of compounding polymers include poly(ethylene glycol) and starch. The non-hydroxybutyrate components in the implant may be present in an amount of at least 1 wt %, at least 5 wt %, at least 10 wt %, at least 15 wt %, at least 25 wt %, at least 50 wt %, at least 75 wt %, or at least 90 wt % of the implant. In some embodiments, the implant includes the hydroxybutyrate and/or conjugate acid of a hydroxybutyrate in an amount of less than or equal to 99 wt %, less than or equal to 75 wt %, less than or equal to 50 wt %, less than or equal to 25 wt %, less than or equal to 10 wt %, or less than or equal to 5 wt % of the implant. Combinations of the above-referenced ranges are also possible. Other ranges are also possible. In some embodiments in which the hydroxybutyrate and/or conjugate acid as well as non-hydroxybutyrate components are present in the form of a body portion, a coating, a solid portion, and/or a layer of a soft tissue repair implant, the body portion, coating, solid portion, and/or layer may include the non-hydroxybutyrate components in an amount specified in one or more of the ranges noted above.

When a soft tissue repair implant comprises a portion (e.g., a coating, a solid portion, a body portion, a layer) comprising a hydroxybutyrate and/or a conjugate acid of a hydroxybutyrate, the portion comprising the hydroxybutyrate and/or a conjugate acid may have a variety of suitable thicknesses. In some embodiments, the portion (e.g., a coating, a solid portion, a body portion, a layer) has a thickness of greater than or equal to 50 nm, greater than or equal to 100 nm, greater than or equal to 200 nm, greater than or equal to 500 nm, greater than or equal to 1 micron, greater than or equal to 2 micron, greater than or equal to 5 microns, greater than or equal to 10 microns, greater than or equal to 50 microns, greater than or equal to 100 microns, greater than or equal to 200 microns, greater than or equal to 500 microns, greater than or equal to 750 microns, greater than or equal to 1 mm, or greater than or equal to 5 mm. In some embodiments, the portion (e.g., a coating, a solid portion, a body portion, a layer) has a thickness of less than or equal to 1 cm, less than or equal to 5 mm, less than or equal to 1 mm, less than or equal to 750 microns, less than or equal to 500 microns, less than or equal to 200 microns, less than or equal to 100 microns, less than or equal to 50 microns, less than or equal to 10 microns, less than or equal to 5 microns, less than or equal to 2 microns, less than or equal to 1 micron, less than or equal to 500 nm, less than or equal to 200 nm, or less than or equal to 100 nm. Combinations of the above-referenced ranges are also possible. Other ranges are also possible.

When the hydroxybutyrate and/or conjugate acid of a hydroxybutyrate is present in the form of a coating, the coating may be formed by any suitable process. In some embodiments, such as for a hydrogel coating, the coating may be formed as described above. In other embodiments, a coating may be formed by dip coating and/or spray coating a formulation onto a body portion. In certain embodiments, a coating may be formed by slot die coating or reverse roll coating. In some embodiments, the thickness of the coating, mechanical integrity, and/or coating uniformity may be tailored by varying the parameters of the coating method used. Other methods of forming coatings are also possible.

Several aspects of the coating method can be controlled. When coating a very thin layer, mechanical integrity may be improved by coating uniformity. Both particulate contamination and undesired precipitation from solution can lead to poor mechanical properties in the final coating. To prevent these defects, several steps can be taken. For example, a method may involve keeping the surface to be coated with substantially free of static charging, which can affect the adhesion of the coating to that surface, and can additionally attract unwanted particulate contaminants on the surface. Static charging can be reduced or eliminating by applying static strings to the substrate during unwinding, or controlling the electronic state of the coat rolls (e.g., attached to ground, floating, biased). A method may also be employed to prevent unwanted precipitation out of the coating solution, e.g., by employing continuous mixing to prevent coagulation. Other techniques are also known to those by ordinary skill in the art.

In one set of embodiments, slot die coating is used to form a coating on a surface (e.g., of a body portion). In slot die coating, a fluid is delivered by a pump to a die which in turn delivers the coating fluid to the desired substrate. The die will usually include three pieces: a top, a bottom, and an internal shim. Either the top or bottom may include a well or reservoir to hold fluid and spread it across the width of the die. The shim determines both the size of the gap between the top and bottom plates as well as defining the coating width.

Thickness of the coating in this case may depend mainly on three factors: the rate at which fluid is delivered to the die (pump speed), the speed at which the substrate is moving past the die lips (line speed), and the size of the gap in the die lips (slot height). Thickness will additionally depend on the inherent properties of the solution to be coated such as viscosity and percent solids.

The uniformity of the coating will be directly related to how well the internal manifold in the die distributes the fluid across the substrate. To control coating uniformity, several steps can be taken. For example, the shape of the reservoir supplying the fluid can be adjusted to equalize pressure across the width of the die. The shape of internal shim can be adjusted to account for pressure variations due to the position of the fluid inlet. The internal shim thickness can also be adjusted to produce higher or lower pressure drops between the fluid inlet and the die lips. The pressure drop will determine the residence time of the fluid in the die and can be used to influence coating thickness and prevent problems such as dry out in the die.

In another set of embodiments, reverse roll coating is used to form a coating on a surface (e.g., of a body portion). In one embodiment, a three roll reverse roll coater fluid is picked up by a first roller (metering roller), transferred in a controlled fashion to a second roller (application roller), and then wiped off of the second roller by the substrate as it travels by. More rollers can be used employing a similar technique. The coating fluid is delivered to a reservoir by a pump; the metering roller is positioned so that it is partially submerged in the coating fluid when the pan is filled. As the metering roller spins the application roller is moved (or vice versa) so that fluid is transferred between the two.

The amount of fluid, and in turn the final coat thickness of the coating, is partially determined by the amount of fluid transferred to the application roller. The amount of fluid transfer can be affected by changing the gaps between the rollers or by applying a doctor blade at any point in the process. Coating thickness is also affected by line speed in a way similar to slot die coating. Coating uniformity in the case of reverse roll coating may depend mainly on the uniformity of the coat rolls and the doctor blade(s) if any are used.

Figure 2C:
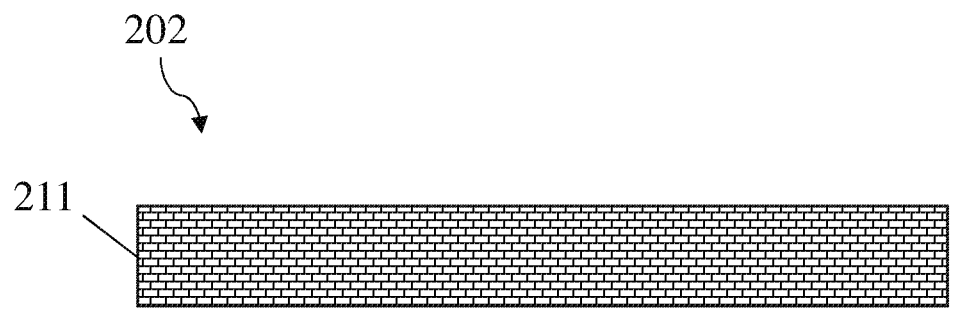
FIG. 2C is a cross-sectional schematic illustration of a soft tissue repair implant comprising a fabric portion and a hydroxybutyrate and/or a conjugate acid of a hydroxybutyrate, according to some embodiments of the invention.

In some embodiments, a soft tissue repair implant may comprise a hydroxybutyrate and/or a conjugate acid of a hydroxybutyrate that is part of a fabric portion. For example, the hydroxybutyrate and/or conjugate acid of a hydroxybutyrate may be a component of a fabric portion (e.g., a fabric layer) within the soft tissue repair implant. FIG. 2C shows one non-limiting embodiment of a soft tissue repair implant in which a soft tissue implant 202 comprises a fabric portion 211 comprising a hydroxybutyrate and/or a conjugate acid of a hydroxybutyrate. In certain embodiments, the hydroxybutyrate and/or the conjugate acid of the hydroxybutyrate may be a component of the fibers of the fabric portion. For example, the hydroxybutyrate and/or conjugate acid of the hydroxybutyrate may be co-extruded with fibers of another material (e.g., a polymeric material) to form fibers of the fabric portion. As a second example, a fabric portion may comprise one or more fibers to which the hydroxybutyrate and/or the conjugate acid of the hydroxybutyrate are covalently bonded. In some embodiments, the fibers may be chemically functionalized prior to bonding. As a third example, the fabric portion may be a foam that comprises the hydroxybutyrate and/or the conjugate acid of the hydroxybutyrate. As a fourth example, the hydroxybutyrate and/or the conjugate acid of the hydroxybutyrate may be co-knitted with one or more fibers of the fabric portion (e.g., with one or more poly(propylene) fibers within the fabric portion). The hydroxybutyrate and/or conjugate acid of the hydroxybutyrate may be provided throughout the soft tissue repair implant 202, or at one or more portions of the soft tissue repair implant 202.

Figure 3A:
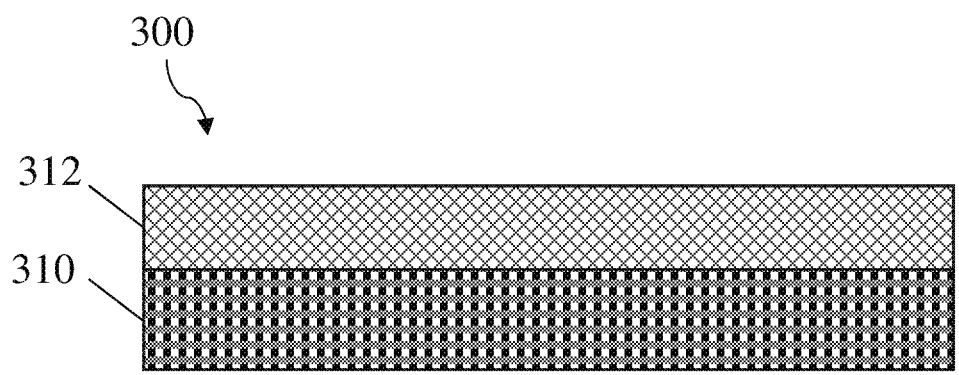
FIG. 3A is a cross-sectional schematic illustration of a soft tissue repair implant comprising a first body portion layer and a second body portion layer, according to some embodiments of the invention.
Figure 3B:
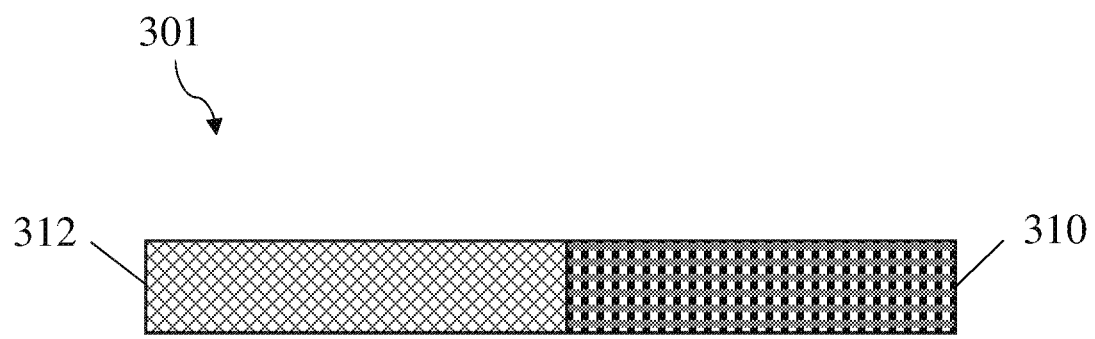
FIG. 3B is a cross-sectional schematic illustration of a soft tissue repair implant comprising a first body portion layer and a second body portion layer, according to some embodiments of the invention.

In some embodiments, a soft tissue repair implant may comprise two or more body portion layers. For example, the soft tissue repair implant may further comprise a second body portion layer, a third body portion layer, or more body portion layers. FIG. 3A shows one non-limiting embodiment of a soft tissue repair implant 300 comprising a first body portion layer 310 and a second body portion layer 312. It should be appreciated that multiple body portion layers within a soft tissue repair implant may be oriented in a variety of suitable manners with respect to each other. In some embodiments, such as shown illustratively in FIG. 3A, one body portion layer (e.g., a second body portion layer) may be adjacent to, or lie on top of, another body portion layer (e.g., a first body portion layer). In other embodiments, such as shown in FIG. 3B, two body portion layers may be positioned side by side. Optionally, at least portions of the two body portion layers may overlap with one another. In some embodiments, the body portions are fabric portions (e.g., fabric layers).

It should be appreciated that if a soft tissue repair implant comprises more than one body portion layer, the different body portion layers that make up the soft tissue repair implant may have similar properties to each other or may have different properties from each other. For example, in some cases a soft tissue repair implant may comprise two or more layers that are substantially identical, and therefore have substantially identical properties (e.g., type of body portion materials, characteristics of components (such as fibers, if present) within the body portion, porosity, and the like). As another example, a soft tissue repair implant may be formed entirely from layers that are substantially identical. As a third example, a soft tissue repair implant may be comprise two or more layers that are substantially different from each other in one or more, or all, properties (e.g., type of body portion materials, characteristics of components (such as fibers, if present) within the body portion, porosity, and the like).

When a soft tissue repair implant comprises two or more body portion layers, the two or more body portion layers may be joined together in a variety of suitable manners. In some embodiments, one or more body portion layers within a soft tissue repair implant may be bonded together using an adhesive, or joined by stitching, heat fusion, plasma treatment, or other approaches as would be apparent to one of skill in the art.

When a soft tissue repair implant comprises more than one body portion layer, it should be understood that a hydroxybutyrate and/or a conjugate acid of a hydroxybutyrate may be provided as a component of one or more of the body portion layers and/or may be provided as a coating on one or more of the body portion layers as described above. As an example, the hydroxybutyrate and/or the conjugate acid of a hydroxybutyrate may be a component of a coating disposed on an outermost body portion layer and/or conformally coating one or more surfaces in an outermost body portion layer. As a second example, the hydroxybutyrate and/or a conjugate acid of a hydroxybutyrate may be a component of a coating disposed at a surface positioned between two body portion layers. Other configurations of the hydroxybutyrate and/or the conjugate acid of a hydroxybutyrate with respect to body portion layers and coatings thereon are also contemplated.

Figure 4A:
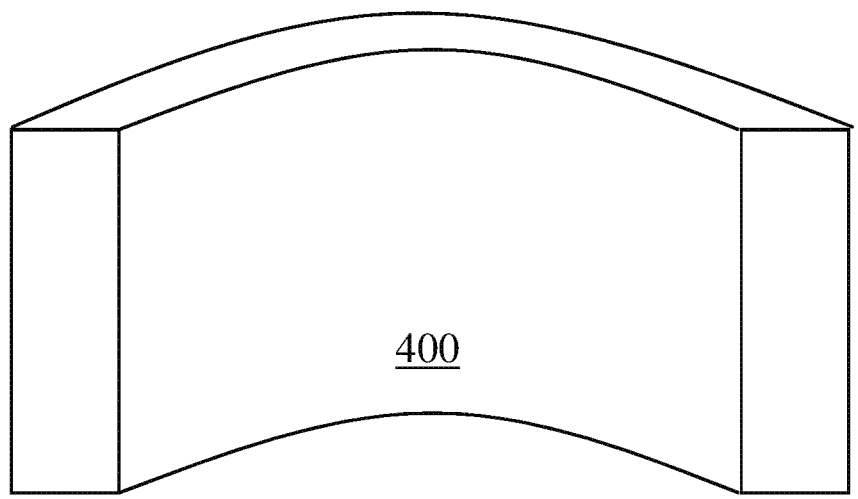
FIG. 4A is a perspective schematic illustration of a soft tissue repair implant with concave curvature, according to some embodiments of the invention.
Figure 4B:
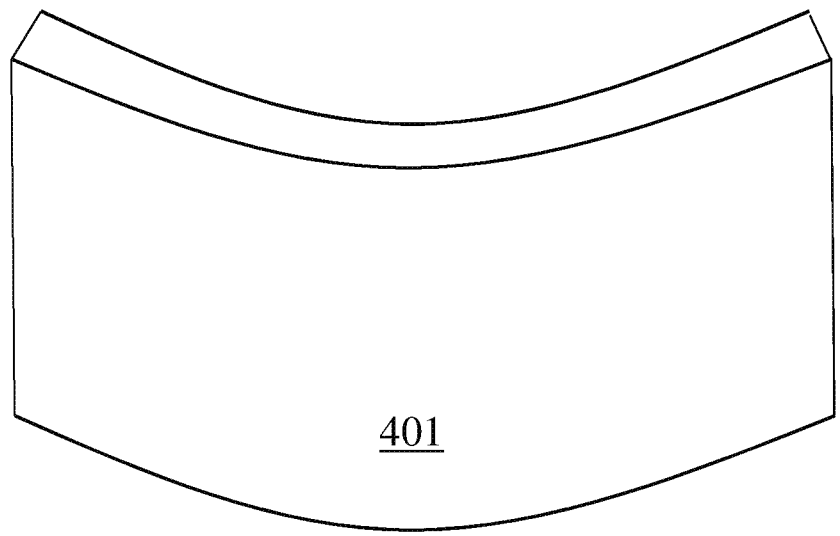
FIG. 4B is a perspective schematic illustration of a soft tissue repair implant with convex curvature, according to some embodiments of the invention.
Figure 4C:
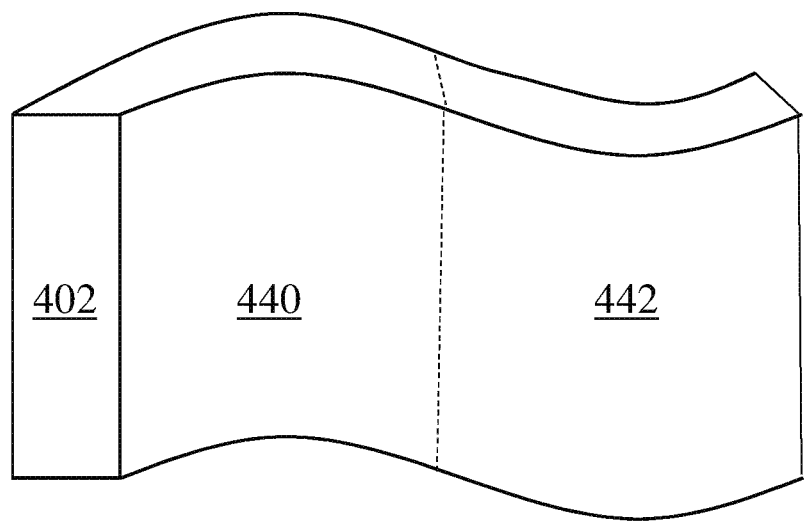
FIG. 4C is a perspective schematic illustration of a soft tissue repair implant comprising a portion with convex curvature and a portion with concave curvature, according to some embodiments of the invention.
Figure 4D:
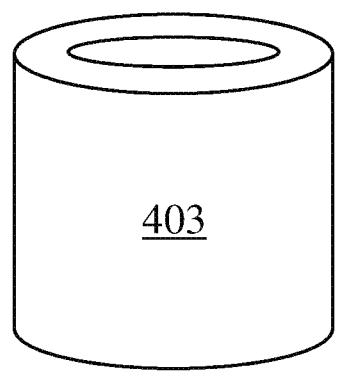
FIG. 4D is a perspective schematic illustration of a soft tissue repair implant with a 3-dimensional shape, according to some embodiments of the invention.

In certain embodiments, a soft tissue repair implant (e.g., a body portion) may have a generally planar shape, e.g., as shown illustratively in FIGS. 1-3. In other embodiments, the soft tissue repair implant (e.g., a body portion) may be curved, or may comprise a portion that is curved. The curvature of the soft tissue repair implant or portion thereof may be convex, concave, or both. FIGS. 4A-4C show non-limiting embodiments of soft tissue implants 400, 401, and 402. Soft tissue repair implant 400 has concave curvature; soft tissue repair implant 401 has convex curvature; and soft tissue repair implant 402 comprises portion 440 with concave curvature and portion 442 with convex curvature. In certain cases, the soft tissue repair implant may be in the form a solid 3-dimensional shape. FIG. 4D shows one non-limiting embodiment of a soft tissue repair implant with a 3-dimensional shape.

Figure 4E:
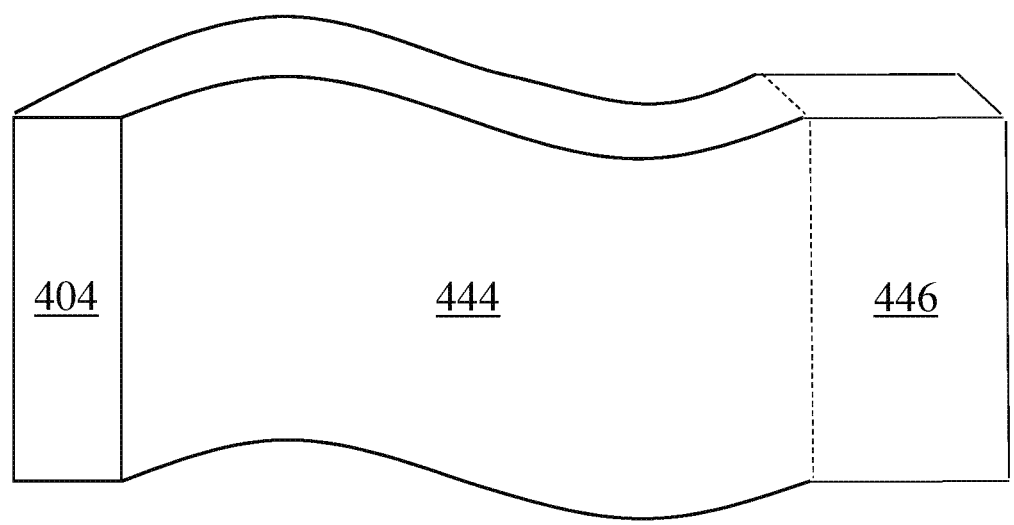
FIG. 4E is a perspective schematic illustration of a soft tissue repair implant comprising a curved portion and a flat portion, according to some embodiments of the invention.

In certain embodiments, a soft tissue repair implant may comprise a portion that is flat and a portion that is curved. FIG. 4E shows one non-limiting embodiment of a soft tissue repair implant 404 comprising curved portion 444 and flat portion 446. It should be understood that the curvature of the curved portion of the soft tissue repair implant depicted in FIG. 4E is exemplary and that other curvatures are also contemplated. For instance, the curved portion may be exclusively convex or exclusively concave. In some embodiments, a soft tissue repair implant may have multiple portions that are flat and multiple portions that are curved.

Figure 5A:
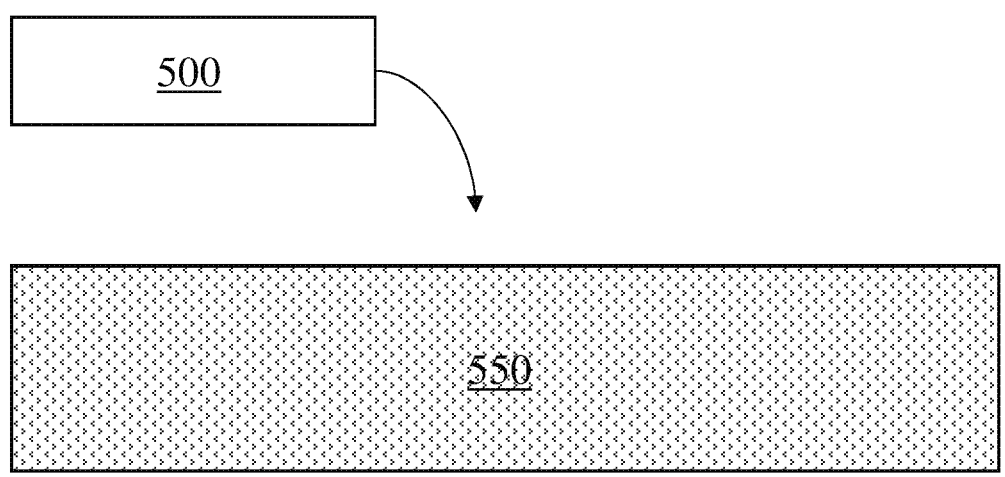
FIGS. 5A-5B are schematic illustrations of a method for implanting a soft tissue repair implant into a soft tissue, according to some embodiments of the invention.
Figure 5B:
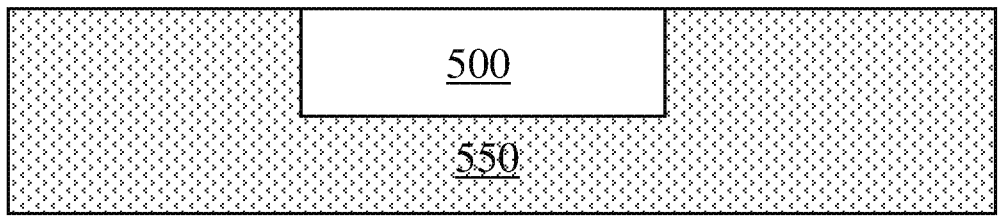
Figure 5C:
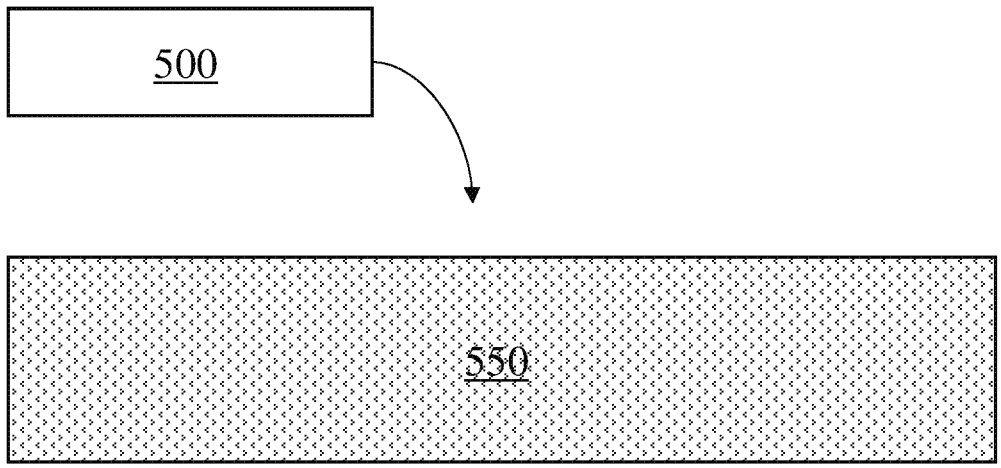
FIGS. 5C-5D are schematic illustrations of a method for implanting a soft tissue repair implant onto a soft tissue, according to some embodiments of the invention.
Figure 5D:
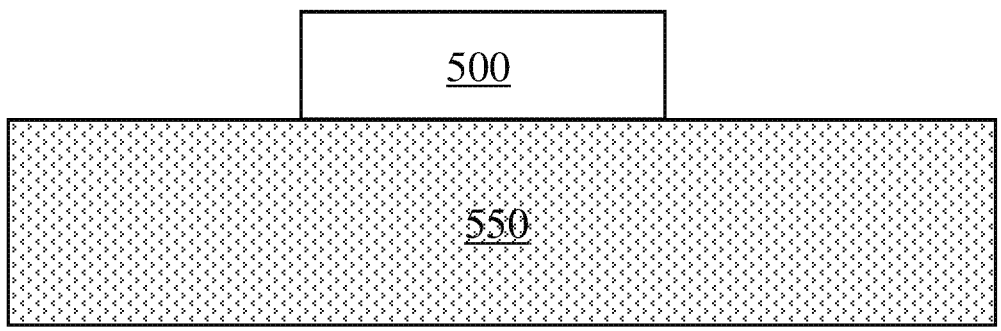

In some embodiments, a soft tissue repair implant may be implanted into a patient adjacent the soft tissue to be repaired. FIGS. 5A and 5B show one non-limiting embodiment of a method in which a soft tissue repair implant 500 is implanted into a soft tissue 550. FIGS. 5C and 5D show one non-limiting embodiment of a method in which soft tissue repair implant 500 is implanted on soft tissue 550. Although FIGS. 5A-5B and 5C-5D are shown as different processes, in certain embodiments a soft tissue repair implant may be implanted both in and on a soft tissue. For example, a soft tissue repair implant may be partially implanted into a soft tissue and partially extend over the soft tissue after implantation. The soft tissue repair implant may be used for a variety of applications, such as treating a hernia (e.g., inguinal hernia, femoral hernia, incisional hernia, ventral hernia, hiatal hernia). The soft tissue may be any suitable type of soft tissue, such as the abdominal wall, or a connective tissue (e.g. an interstitial connective tissue, a parietal connective tissue, a synovial membrane, a tendon sheath, a peritoneal serosa, a pleural serosa). A soft tissue repair implant may be implanted by a variety of suitable methods. In some embodiments, the soft tissue repair implant may be implanted in open surgery, minimally invasive surgery or a hybrid of open surgery and minimally invasive surgery.

As described above, certain embodiments relate to soft tissue implants that comprise one or more fabric portion(s) and/or layers. The fabric portion(s) and/or layer(s) may comprise a variety of suitable types of fabrics, such as a knit fabric, a woven fabric, a non-woven fabric, a braided fabric, an extruded fabric, and/or a cast fabric. "Fabric" for purposes of this patent is to be broadly construed and includes porous, micro-porous and solid fabrics, and combinations of any of the foregoing.

In embodiments in which one or more fabric portions (e.g., fabric layers) within a soft tissue repair implant comprise fibers, the fibers may have a variety of suitable average lengths. In some embodiments, one or more fabric portions may comprise continuous fibers (e.g., fibers formed from a continuous process such as a meltblowing process, a spinning process).

In embodiments in which one or more fabric portions (e.g., fabric layers) within a soft tissue repair implant comprise fibers, the fibers may have a variety of suitable chemical compositions. In some embodiments, one or more of the fabric portion(s) may comprise fibers that are biocompatible, such as fibers that are non-toxic. In certain cases, one or more of the fabric portion(s) may comprise biocompatible fibers that are resorbable, such as poly(glycolic acid) fibers, poly(lactic acid) fibers, poly(dioxanone) fibers, poly(caprolactone) fibers, polyhydroxyalkanoate fibers (e.g., poly-2-hydroxybutyrate fibers, poly-3-hydroxybuytrate fibers, poly-4-hydroxybutyrate fibers), calcium alginate fibers, poly(glactin) (VICRYL™) fibers, poly(glycolic acid) (DEXON™) fibers. In certain cases, one or more of the fabric portion(s) may comprise biocompatible fibers that are non-resorbable, such as polypropylene and poly(ethylene terephthalate). Fibers within a fabric portion (e.g., resorbable fibers, non-resorbable fibers) may be synthetic fibers, or may be natural fibers. Accordingly, the soft tissue repair implant may be resorbable or non-resorbable.

In some embodiments in which a soft tissue repair implant comprises one or more body portions (e.g., body portion layers), one or more of the body portions may be a solid body portion (e.g., an extruded polymer portion). In some embodiments, a soft tissue repair implant may comprise one or more body portions that are not solid body portions. It should be appreciated that the soft tissue repair implant may comprise both a solid body portion and a body portion that is not a solid body portion in some cases.

In certain embodiments, a soft tissue repair implant comprises a body portion, such as a solid body portion (e.g., a solid body portion layer), having a solidity of at least 1%, at least 5%, at least 10%, at least 15%, at least 25%, at least 50%, at least 75%, or at least 90%. In some embodiments, the solidity of the body portion is less than or equal to 99%, less than or equal to 75%, less than or equal to 50%, less than or equal to 25%, less than or equal to 10%, or less than or equal to 5%. Combinations of the above-referenced ranges are also possible. Other ranges are also possible.

In certain embodiments, one or more body portions (e.g., body portion layers) comprises pores. When present, at least a portion of the pores may be externally-accessible pores, and/or at least a portion of the pores may be completely enclosed pores.

In some cases, a soft tissue repair implant may comprise a body portion comprising pores and a body portion that does not include pores or does not include pores in an appreciable amount (e.g., a solid body portion).

In certain embodiments, a soft tissue repair implant may comprise a body portion that is at least partially infiltratable by cells and/or tissues. In some embodiments, the tissue that may be capable of infiltrating into the body portion may be muscle tissue. For example, the soft tissue repair implant may comprise pores that are externally-accessible or are interconnected, may have pores that are of an appropriate size to be accessed by cells, may have a surface chemistry that is favorable for cell attachment and/or spreading, may be capable of serving as a supportive matrix that cells can colonize, and the like.

In certain embodiments, a soft tissue repair implant may comprise a body portion that is not tissue infiltratable, or which is minimally tissue infiltratable.

A soft tissue repair implant may comprise both a body portion that is at least partially tissue infiltratable and a body portion that is not tissue infiltratable or is minimally tissue infiltratable in some embodiments.

In certain embodiments, a soft tissue repair implant may comprise a body portion that is at least partially resorbable.

In certain embodiments, a soft tissue repair implant may comprise a body portion that is not resorbable, or which is minimally resorbable.

It should be understood that a soft tissue repair implant may comprise both a body portion that is at least partially resorbable and a body portion that is not resorbable.

In some embodiments, a soft tissue repair implant may comprise one or more body portions that are biocompatible. The body portion(s) may be formed from biocompatible materials, and/or may have minimal or no toxicity. In some embodiments, a soft tissue repair implant may include only body portions that are biocompatible. In some embodiments, a soft tissue repair implant may comprise one or more body portions that comprise a synthetic material (such as those as described above). In some embodiments, a soft tissue repair implant may comprise one or more body portions that comprise a natural material. It should be appreciated that a soft tissue repair implant may comprise exclusively synthetic materials, exclusively natural materials, or both synthetic materials and natural materials.

In certain embodiments, a body portion within a soft tissue repair implant may be one or more of BARD MESH (available from C.R. Bard, Inc.), SOFT TISSUE PATCH, SURGIPRO™, TRELEX™, PROLENE® and MERSILENE®, and other soft tissue repair implant arrangements.

Non-limiting examples of suitable soft tissue repair implants (e.g., body portions) include XENMATRIX™, COLLAMEND™, ALLOMAX™ (available from C.R. Bard, Inc.), COOK SURGISIS™, 3DMAX™ Mesh, 3DMAX™ Light Mesh, BARD® Soft Mesh, BARD® Mesh Flat Sheets, COMPOSIX™ E/X Mesh, COMPOSIX™ L/P Mesh, DULEX™ Mesh, KUGEL™ Hernia Patch, MK™ Patch, ONFLEX™ Mesh, PERFIX™ Light Plug, PERFIX™ Plug, SEPRAMESH™ IP Composite, VENTRALEX™ Hernia Patch, VENTRALEX™ ST Hernia Patch, VENTRALIGHT™ ST Mesh, VENTRIO™ Hernia Patch, VENTRIO™ ST Hernia Patch, and VISILEX™ Mesh.

The soft tissue repair implant may have a variety of suitable burst strengths. In some embodiments, a soft tissue repair implant may have a burst strength of at least 4 pounds force (lbf), at least 5 lbf, at least 5.7 lbf, at least 6 lbf, at least 8 lbf, at least 10 lbf, at least 15 lbf, at least 20 lbf, at least 25 lbf, at least 50 lbf, at least 75 lbf, at least 100 lbf, at least 150 lbf, at least 200 lbf, at least 250 lbf, at least 300 lbf, at least 350 lbf, at least 400 lbf, or at least 450 lbf. The soft tissue repair implant may have a burst strength of less than or equal to 500 lbf, less than or equal to 450 lbf, less than or equal to 400 lbf, less than or equal to 350 lbf, less than or equal to 300 lbf, less than or equal to 250 lbf, less than or equal to 200 lbf, less than or equal to 150 lbf, less than or equal to 100 lbf, less than or equal to 75 lbf, less than or equal to 50 lbf, less than or equal to 25 lbf, less than or equal to 20 lbf, less than or equal to 15 lbf, or less than or equal to 10 lbf. Combinations of the above-referenced ranges are also possible (e.g., greater than or equal to 5 lbf and less than or equal to 500 lbf). Other ranges are also possible. The burst strength may be determined according to the standard TM3791148, rev 2 using a ⅜ inch diameter burst probe and a circular test area of 1.0 inch.

The following examples are intended to illustrate certain embodiments of the present invention, but do not exemplify the full scope of the invention.

Example 1

This Example compares the effect of 4-hydroxybutyrate on the expression of cathelicidin LL-37 with the effect of other molecules, salts, and solubilized biological scaffolds on the expression of cathelicidin LL-37.

Primary macrophages were differentiated from mononuclear cells harvested from the bone marrow of C57bl/6 mice. A solution of these primary macrophages was divided into 18 wells, each of which was exposed for 18 hours to one of samples nos. 1-18; i.e., a composition comprising either a species of interest dissolved in cell growth media or a solubilized biological scaffold dissolved in cell growth media. The cell growth media was HyClone™ Dulbecco's High Glucose Modified Eagles Medium (DMEM) (GE Healthcare Life Sciences, No. SH30243FS) supplemented with 10 vol %/vol Fetal Bovine Serum (FBS) (Atlanta Biologicals No. S 11150) and 100 µg/mL Penicillin/100 µg/mL Streptomycin (GE Healthcare Life Sciences, No. SV30010).

After exposure of the macrophages to the samples, the macrophages were prepared for cathelicidin LL-37 immunolabeling by the following procedure. First, the macrophages stimulated by the protocol described above were fixed in 2 wt %/vol paraformaldehyde in phosphate buffered saline (PBS) for 30 minutes. Then, the macrophages were washed with PBS. After these steps, the macrophages were incubated for one hour with a blocking buffer (2 vol %/vol goat serum, 1 wt %/vol bovine serum albumin, 0.1 vol %/vol triton X-100, and 0.1 vol %/vol tween-20 in PBS) to inhibit non-specific binding antibodies. Then, the macrophages were incubated overnight at 4° C. in primary antibody polyclonal rabbit anti-Cathelicidin (Abbiotec, Cat. No. 253814) at a 1:100 dilution in the blocking buffer described above. The next day, the macrophages were washed in PBS and then incubated for one hour at room temperature in fluorophore-conjugated secondary antibody (Alexa Fluor goat anti-rabbit 488; Cat. No. A11034, Invitrogen) at a 1:200 dilution in the blocking buffer described above. The macrophages were then washed in PBS again, after which the nuclei were counterstained with 4'-6-diamidino-2-phenylindole (DAPI) for 5 minutes. Finally, the macrophages were again washed with PBS.

After immunolabeling preparation, images were taken of the counterstained macrophages for three 20× fields for each well using a Zeus live-cell microscope. First, samples no. 1-3 were imaged at a variety of light exposure times. The light exposure time that produced the best images was determined, and the remaining samples were imaged at this light exposure time.

Figure 6:
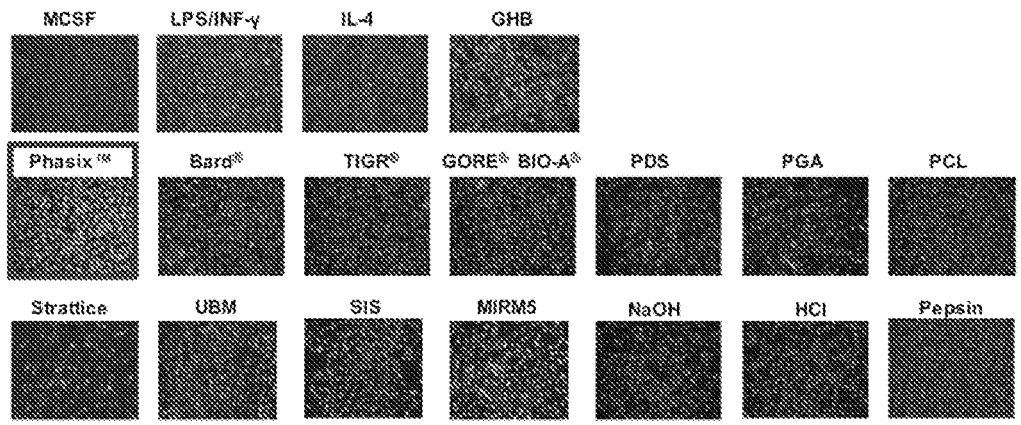
FIG. 6 is a composite image of several micrographs showing immunolabeling images, according to some embodiments of the invention.
Figure 7:
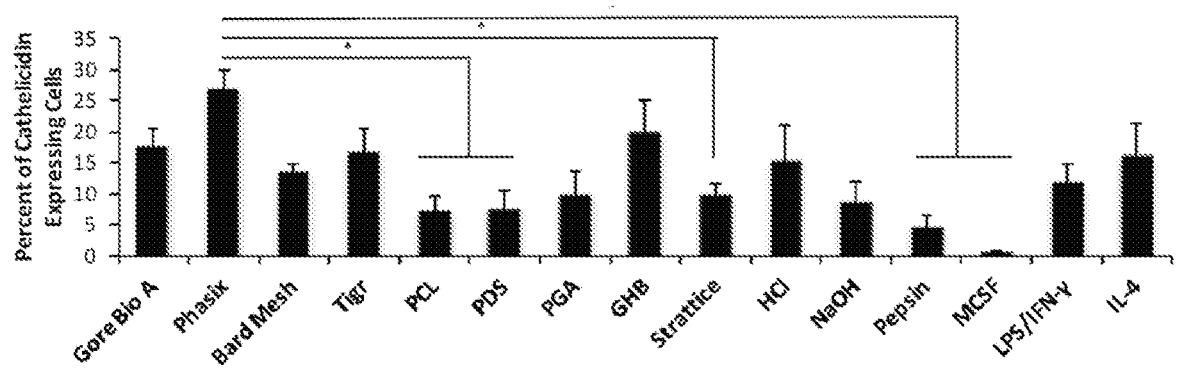
FIG. 7 is a bar chart showing cathelicidin LL-37 expression for several samples, according to some embodiments of the invention.

Table 1 lists each sample, FIG. 6 shows the immunolabeling images, and FIG. 7 shows the calculated percent of cathelicidin LL-37 expressing cells for each sample. After immunolabeling, each macrophage nucleus appeared blue in the immunolabeling images and cathelicidin LL-37 appeared green. The percentages of macrophages expressing cathelicidin LL-37 shown in FIG. 7 were calculated by dividing the number of cathelicidin LL-37-expressing cells in each image (determined by the number of blue nuclei located in close proximity to green cathelicidin LL-37) by the number of cells in each image (determined by the number of blue nuclei in each image). The identification of cathelicidin LL-37 and cell nuclei in the images was determined with the aid of CellProfiler, a commercial software analyzer (available at http://www.cellprofiler.org). CellProfiler. (N=3, triplicates, Values: Mean±SEM, *p<0.05). FIG. 6 and FIG. 7 show that 4-hydroxybutyrate strongly promoted cathelicidin LL-37 expression.

TABLE 1

| Sample No. | Species of interest or biological scaffold | Scaffold composition | Lot No. | Concentration of species of interest or biological scaffold |
|---|---|---|---|---|
| 1 | Macrophage colony-stimulating factor (MCSF) - Untreated control | | | N/A |
| 2 | Lipopolysaccharide and interferon-γ (LPS/IFN-γ) | | | 100 ng/ml LPS 20 ng/ml IFN-γ |
| 3 | Interleukin-4 (IL-4) | | | 20 ng/mL |
| 4 | 4-hydroxybutyrate (4HB) | | | 12 mM |
| 5 | Hydrochloric acid-solubilized Phasix scaffold | Poly(4-hydroxybutyrate) | HUYKTP18 HUAR0501 HUYDTP08 | 1.32 mg/mL |
| 6 | Hydrochloric acid-solubilized Bard scaffold | Poly(propylene) | HUAV0936 HUYL0855 HUAP0728 | 1.32 mg/mL |
| 7 | Sodium hydroxide-solubilized TIGR scaffold | Trimethylene carbonate, glycolate, lactate | 144143437-02 151011619-04 162044 | 1.32 mg/mL |
| 8 | Sodium hydroxide-solubilized GORE BIO-A scaffold | Trimethylene carbonate, glycolate | 13348678 12669212 14484673 | 1.32 mg/mL |
| 9 | Hydrochloric acid-solubilized Poly(dioxanone) scaffold (PDS) | Poly(dioxanone) | | 1.32 mg/mL |
| 10 | Sodium hydroxide-solubilized poly(glycolide) scaffold (PGA) | Poly(glycolide) | | 1.32 mg/mL |
| 11 | Sodium hydroxide-solubilized poly(caprolactone) scaffold (PCL) | Poly(caprolactone) | | 1.32 mg/mL |
| 12 | Pepsin-solubilized Strattice scaffold | Porcine-derived decellularized dermal extracellular matrix (ECM) | SP100386-160 SP100386-161 SP100386-163 | 200 µg/mL |
| 13 | Pepsin-solubilized UBM scaffold | Porcine-derived decellularized urinary bladder matrix | | 200 µg/mL |
| 14 | Pepsin-solubilized SIS mesh | Porcine-derived decellularized small intestinal submucosa | | 200 µg/mL |
| 15 | Pepsin-solubilized MIRM5 mesh | Porcine-derived decellularized dermal ECM | | 200 µg/mL |
| 16 | Sodium hydroxide | | | 1.32 mg/mL |
| 17 | Hydrochloric acid | | | 1.32 mg/mL |
| 18 | Pepsin | | | 200 µg/mL |

Example 2

This Example compares the effects of 4-hydroxybutyrate, 2-hydroxybutyrate, 3-hydroxybutyrate, butyrate, and Phasix mesh on the expression of cathelicidin LL-37.

Figure 8:
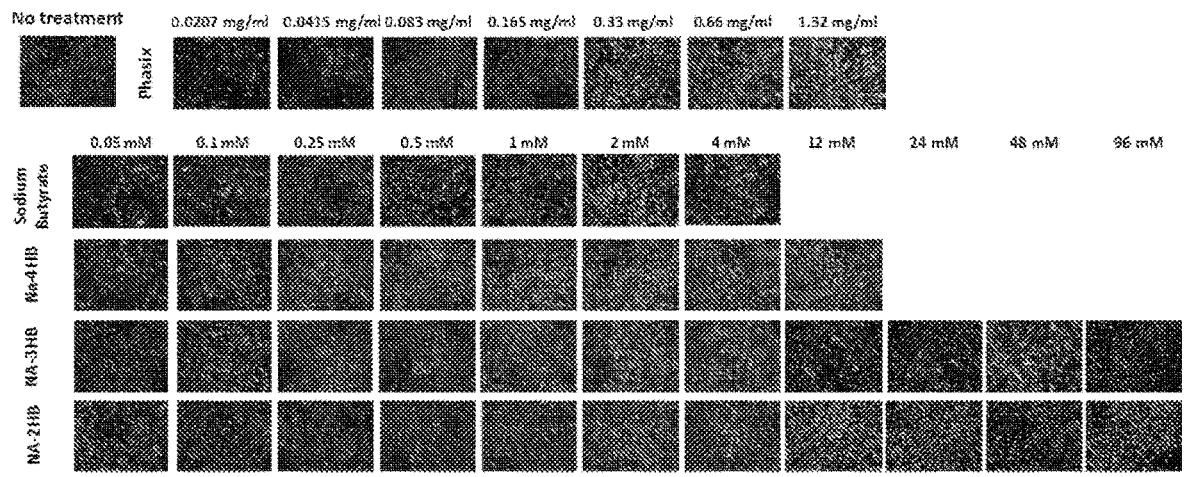
FIG. 8 is a composite image of several micrographs showing immunolabeling images, according to some embodiments of the invention.
Figure 8:
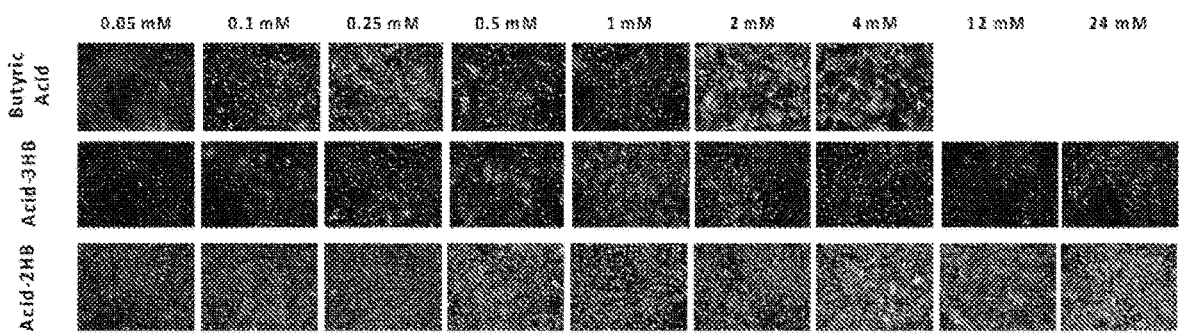
Figure 9:
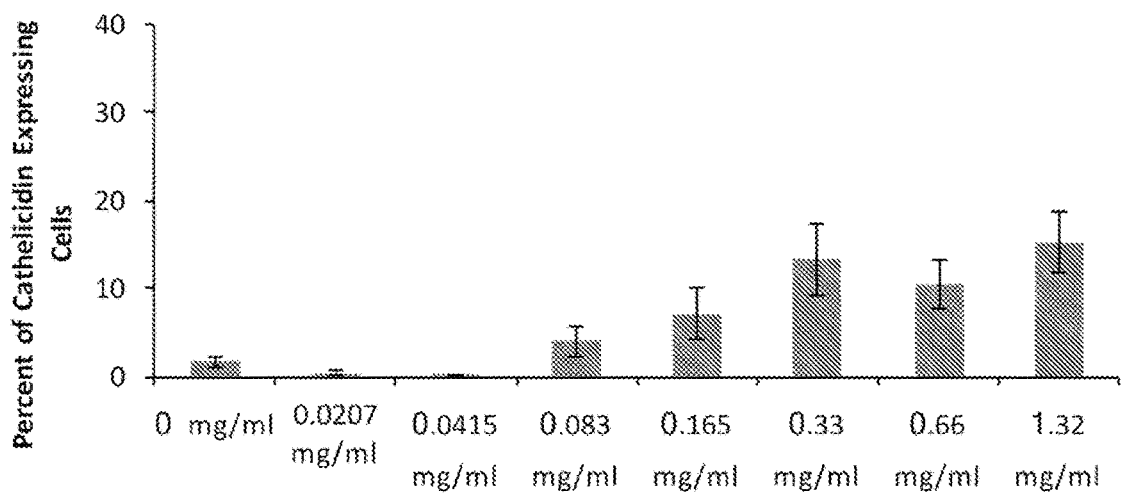
FIGS. 9-16 are bar charts showing cathelicidin LL-37 expression for several samples, according to some embodiments of the invention.
Figure 10:
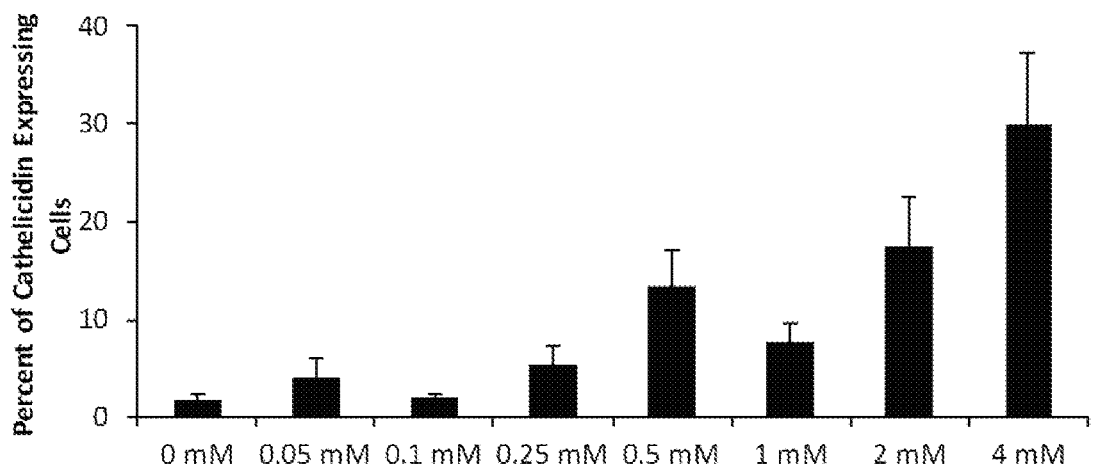
Figure 11:
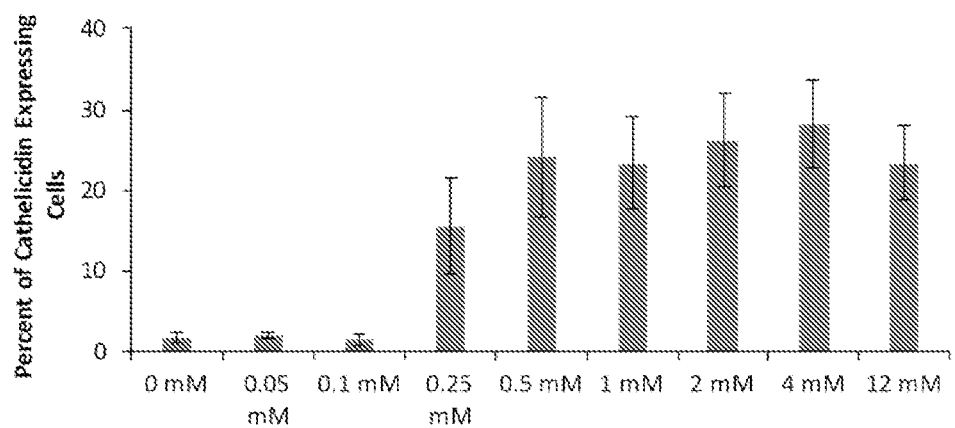
Figure 12:
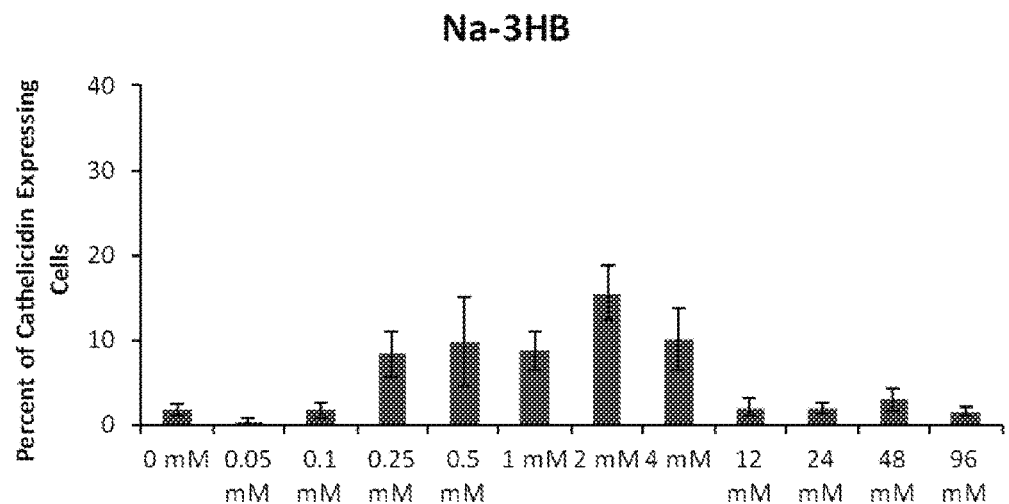
Figure 13:
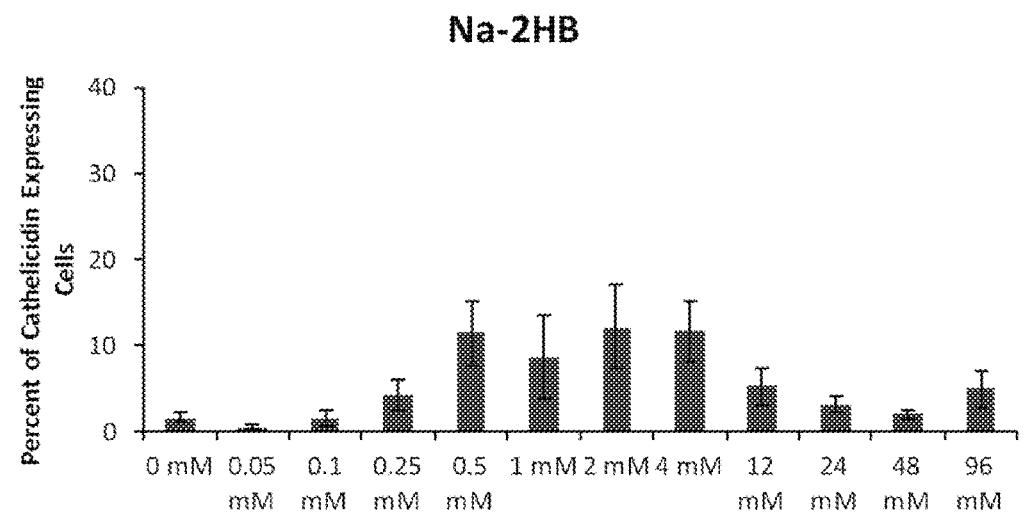
Figure 14:
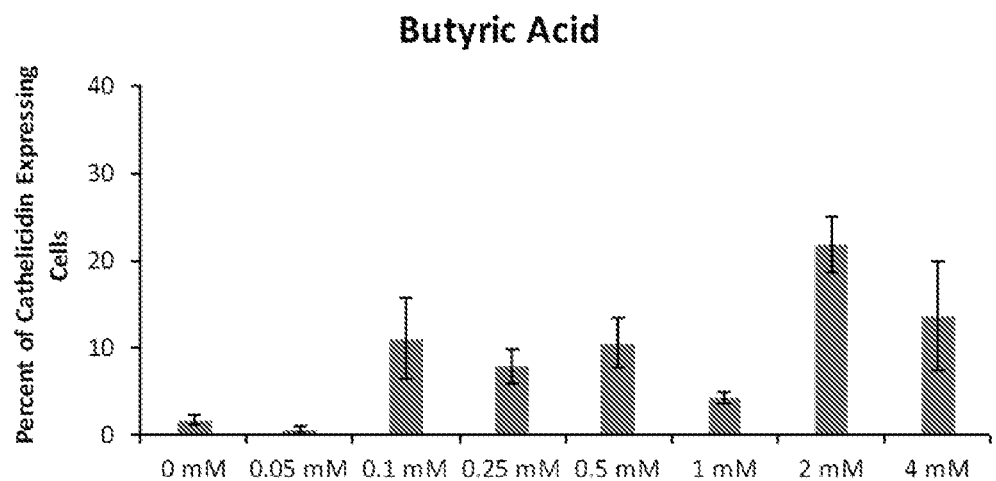
Figure 15:
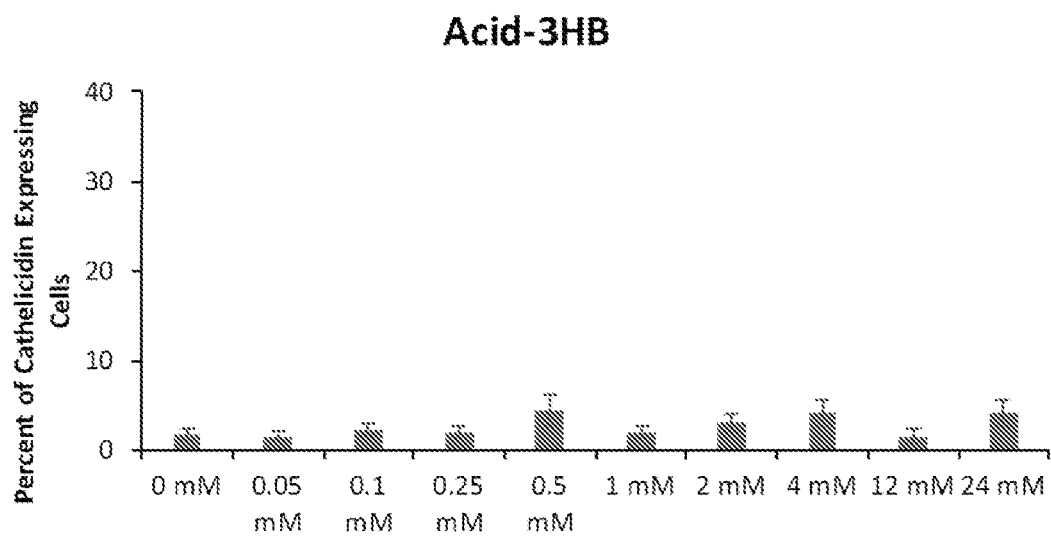
Figure 16:
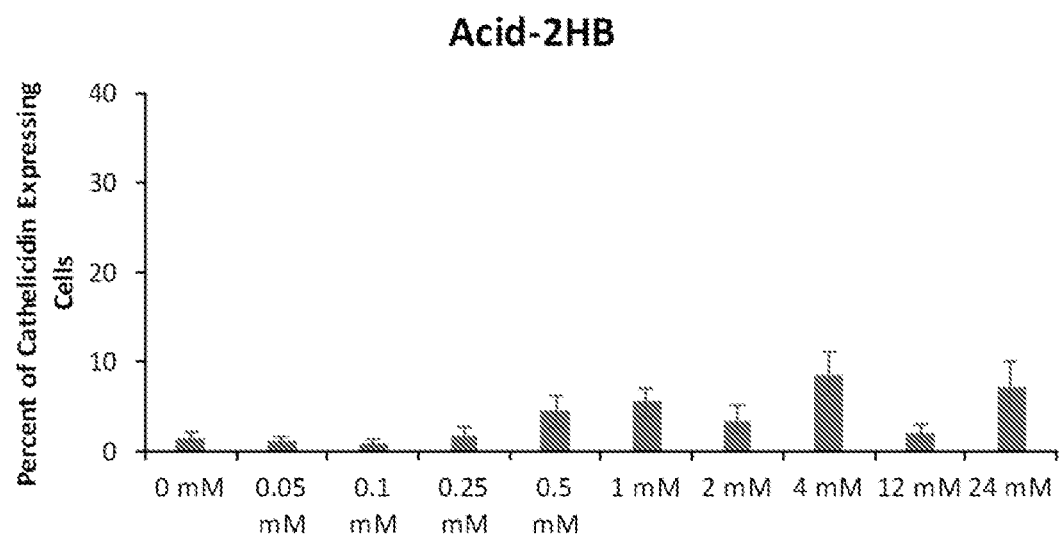

Primary macrophages were differentiated from mononuclear cells harvested from the bone marrow of C57bl/6 mice. A solution of these primary macrophages was divided into 70 wells, each of which was exposed for 18 hours to one of compositions nos. 1-70; i.e., a control composition or a composition comprising one of hydrochloric acid-solubilized Phasix mesh, sodium butyrate, sodium 4-hydroxybutyrate (GHB or 4HB), sodium 3-hydroxybutyrate (PHB or 3HB), sodium 2-hydroxybutyrate (αHB or 2HB), butyrate, butyric acid, 3-hydroxybutyric acid, and 2-hydroxybutyric acid. After this step, the macrophages were prepared for cathelicidin LL-37 immunolabeling imaging in the same manner as described in Example 1, and immunolabeling images of cathelicidin LL-37 were produced in the same manner as described in Example 1. Table 2 shows each composition. FIG. 8 shows the immunolabeling images, and FIGS. 9-16 show the calculated percent of cathelicidin LL-37 expressing cells for each sample. The calculated percent of cathelicidin LL-37 in each sample was determined in the same manner as described in Example 1. These Figures show that hydroxybutyrates, such as 4-hydroxybutyrate, effectively induce cathelicidin LL-37 expression.

TABLE 2

| Composition No. | Species of interest | Concentration of species of interest |
|---|---|---|
| 1 | None (control) | N/A |
| 2 | Phasix | 0.0207 mg/mL |
| 3 | Phasix | 0.0415 mg/mL |
| 4 | Phasix | 0.083 mg/mL |
| 5 | Phasix | 0.165 mg/mL |
| 6 | Phasix | 0.33 mg/mL |
| 7 | Phasix | 0.66 mg/mL |
| 8 | Phasix | 1.32 mg/mL |
| 9 | Sodium butyrate | 0.05 mM |
| 10 | Sodium butyrate | 0.1 mM |
| 11 | Sodium butyrate | 0.25 mM |
| 12 | Sodium butyrate | 0.5 mM |
| 13 | Sodium butyrate | 1 mM |
| 14 | Sodium butyrate | 2 mM |
| 15 | Sodium butyrate | 4 mM |
| 16 | Sodium 4-hydroxybutyrate | 0.05 mM |
| 17 | Sodium 4-hydroxybutyrate | 0.1 mM |
| 18 | Sodium 4-hydroxybutyrate | 0.25 mM |
| 19 | Sodium 4-hydroxybutyrate | 0.5 mM |
| 20 | Sodium 4-hydroxybutyrate | 1 mM |
| 21 | Sodium 4-hydroxybutyrate | 2 mM |
| 22 | Sodium 4-hydroxybutyrate | 4 mM |
| 23 | Sodium 4-hydroxybutyrate | 12 mM |
| 24 | Sodium 3-hydroxybutyrate | 0.05 mM |
| 25 | Sodium 3-hydroxybutyrate | 0.1 mM |
| 26 | Sodium 3-hydroxybutyrate | 0.25 mM |
| 27 | Sodium 3-hydroxybutyrate | 0.5 mM |
| 28 | Sodium 3-hydroxybutyrate | 1 mM |
| 29 | Sodium 3-hydroxybutyrate | 2 mM |
| 30 | Sodium 3-hydroxybutyrate | 4 mM |
| 31 | Sodium 3-hydroxybutyrate | 12 mM |
| 32 | Sodium 3-hydroxybutyrate | 24 mM |
| 33 | Sodium 3-hydroxybutyrate | 48 mM |
| 34 | Sodium 3-hydroxybutyrate | 96 mM |
| 35 | Sodium 2-hydroxybutyrate | 0.05 mM |
| 36 | Sodium 2-hydroxybutyrate | 0.1 mM |
| 37 | Sodium 2-hydroxybutyrate | 0.25 mM |
| 38 | Sodium 2-hydroxybutyrate | 0.5 mM |
| 39 | Sodium 2-hydroxybutyrate | 1 mM |
| 40 | Sodium 2-hydroxybutyrate | 2 mM |
| 41 | Sodium 2-hydroxybutyrate | 4 mM |
| 42 | Sodium 2-hydroxybutyrate | 12 mM |
| 43 | Sodium 2-hydroxybutyrate | 24 mM |
| 44 | Sodium 2-hydroxybutyrate | 48 mM |
| 45 | Sodium 2-hydroxybutyrate | 96 mM |
| 46 | Butyric acid | 0.05 mM |
| 47 | Butyric acid | 0.1 mM |
| 48 | Butyric acid | 0.25 mM |
| 49 | Butyric acid | 0.5 mM |
| 50 | Butyric acid | 1 mM |
| 51 | Butyric acid | 2 mM |
| 52 | Butyric acid | 4 mM |
| 53 | 3-hydroxybutyric acid | 0.05 mM |
| 54 | 3-hydroxybutyric acid | 0.1 mM |
| 55 | 3-hydroxybutyric acid | 0.25 mM |
| 56 | 3-hydroxybutyric acid | 0.5 mM |
| 57 | 3-hydroxybutyric acid | 1 mM |
| 58 | 3-hydroxybutyric acid | 2 mM |
| 59 | 3-hydroxybutyric acid | 4 mM |
| 60 | 3-hydroxybutyric acid | 12 mM |
| 61 | 3-hydroxybutyric acid | 24 mM |
| 62 | 2-hydroxybutyric acid | 0.05 mM |
| 63 | 2-hydroxybutyric acid | 0.1 mM |
| 64 | 2-hydroxybutyric acid | 0.25 mM |
| 65 | 2-hydroxybutyric acid | 0.5 mM |
| 66 | 2-hydroxybutyric acid | 1 mM |
| 67 | 2-hydroxybutyric acid | 2 mM |
| 68 | 2-hydroxybutyric acid | 4 mM |
| 69 | 2-hydroxybutyric acid | 12 mM |
| 70 | 2-hydroxybutyric acid | 24 mM |

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A soft tissue repair implant, comprising:
   a polymeric material;
   a body portion comprising the polymeric material, wherein the body portion is in the form of a three-dimensional shape, a planar shape, or a combination of a three-dimensional shape and a planar shape, and
   at least one of a hydroxybutyrate and a conjugate acid of a hydroxybutyrate in a therapeutically-effective amount for reducing or preventing microbial infection, wherein the at least one of a hydroxybutyrate and a conjugate acid of a hydroxybutyrate is part of the body portion and/or is a component of a coating disposed on the body portion,
   wherein the soft tissue repair implant is configured to repair a soft tissue defect, and
   wherein the at least one of the hydroxybutyrate or the conjugate acid of the hydroxybutyrate is a monomer that is not covalently bonded to any other species.

2. A soft tissue repair implant as in claim 1, wherein the at least one of the hydroxybutyrate and the conjugate acid of the hydroxybutyrate is the hydroxybutyrate and is in the form of a salt.

3. A soft tissue repair implant as in claim 1, wherein the soft tissue repair implant comprises the conjugate acid of the hydroxybutyrate.

4. A soft tissue repair implant as in claim 1, wherein the at least one of the hydroxybutyrate and the conjugate acid of the hydroxybutyrate is 4-hydroxybutyrate or a conjugate acid of 4-hydroxybutyrate.

5. A soft tissue repair implant as in claim 1, wherein the at least one of the hydroxybutyrate and the conjugate acid of the hydroxybutyrate is 2-hydroxybutyrate or a conjugate acid of 2-hydroxybutyrate.

6. A soft tissue repair implant as in claim 1, wherein the at least one of the hydroxybutyrate and the conjugate acid of the hydroxybutyrate is 3-hydroxybutyrate or a conjugate acid of 3-hydroxybutyrate.

7. A soft tissue repair implant as in claim 1, wherein the body portion includes a fabric portion.

8. A soft tissue repair implant as in claim 1, wherein the body portion comprises at least one of a knit fabric, a woven fabric, a non-woven fabric, and a braided fabric.

9. A soft tissue repair implant as in claim 1, wherein the body portion comprises pores.

10. A soft tissue repair implant as in claim 1, wherein a thickness of a layer comprising the at least one of hydroxybutyrate and the conjugate acid of the hydroxybutyrate is greater than or equal to 50 nm and less than or equal to 1 cm.

11. A soft tissue repair implant as in claim 1, wherein at least a portion of the soft tissue repair implant is non-resorbable.

12. A soft tissue repair implant as in claim 1, wherein at least a portion of the soft tissue repair implant is resorbable.

13. A soft tissue repair implant as in claim 1, wherein the soft tissue repair implant comprises a natural material.

14. A soft tissue repair implant as in claim 1, wherein the soft tissue repair implant comprises a synthetic material.

15. A soft tissue repair implant as in claim 1, wherein at least a portion of the soft tissue repair implant is tissue infiltratable.

16. A soft tissue repair implant as in claim 1, wherein at least a portion of the soft tissue repair implant is not tissue infiltratable.

17. A soft tissue repair implant as in claim 1, wherein the therapeutically-effective amount of the at least one of hydroxybutyrate and the conjugate acid of the hydroxybutyrate is a component of a coating disposed on the body portion.

18. A soft tissue repair implant as in claim 17, wherein the body portion comprises fibers, and wherein the coating conformally coats at least a portion of the fibers.

19. A soft tissue repair implant as in claim 1, wherein the soft tissue repair implant is a soft tissue repair prosthesis.

* * * * *